US008008013B2

(12) United States Patent
Gaffney et al.

(10) Patent No.: US 8,008,013 B2
(45) Date of Patent: Aug. 30, 2011

(54) PREDICTING AND DIAGNOSING PATIENTS WITH AUTOIMMUNE DISEASE

(75) Inventors: Patrick M. Gaffney, Oklahoma City, OK (US); Kathy L. Moser, Edmond, OK (US)

(73) Assignee: Oklahoma Medical Research Foundation, Oklahoma City, OK (US)

( * ) Notice: Subject to any disclaimer, the term of this patent is extended or adjusted under 35 U.S.C. 154(b) by 0 days.

(21) Appl. No.: 12/272,265

(22) Filed: Nov. 17, 2008

(65) Prior Publication Data
US 2009/0130683 A1    May 21, 2009

Related U.S. Application Data

(60) Provisional application No. 60/988,675, filed on Nov. 16, 2007.

(51) Int. Cl.
*C12Q 1/68* (2006.01)
*C12P 19/34* (2006.01)
*G01N 33/48* (2006.01)

(52) U.S. Cl. ................ 435/6; 435/91.1; 436/63
(58) Field of Classification Search .................. None
See application file for complete search history.

(56) References Cited

U.S. PATENT DOCUMENTS

| | | | |
|---|---|---|---|
| 7,259,179 B2 | 8/2007 | Burns et al. | 514/396 |
| 7,262,199 B2 | 8/2007 | Fraley et al. | 514/259.3 |
| 7,265,134 B2 | 9/2007 | Hartman et al. | 514/326 |
| 7,276,581 B2 | 10/2007 | Yeatman et al. | 530/350 |
| 7,279,469 B2 | 10/2007 | Pierce et al. | 514/227.5 |
| 7,282,504 B2 | 10/2007 | Armistead et al. | 514/275 |
| 2003/0171253 A1 | 9/2003 | Ma et al. | 514/1 |

FOREIGN PATENT DOCUMENTS
WO    WO 2008/041953    4/2008

OTHER PUBLICATIONS

Dieguez-Gonzalez et al. (Arthritis Research and Therapy 2009 vol. 11 p. 42).*
Halushka (Nature Genetics, 1999; 22:239-247).*
Langdahl (Journal of Bone and Mineral Research 2000 vol. 15 p. 402).*
Wall (Nature Reviews Genetics 2003 vol. 4, pp. 587-597).*
Musone et al. (Nature 2008 vol. 40 p. 1062).*
Baechler et al., "Interferon-inducible gene expression signature in peripheral blood cells of patients with severe lupus," *PNAS*, 100:2610-2615, 2003.
Beyaert et al., "A20 and A20-binding proteins as cellular inhibitors of nuclear factor-kappa B-dependent gene expression and apoptosis," *Biochem. Pharmacol.*, 60:1143-1151, 2000.
Boone et al., "The ubiquitin-modifying enzyme A20 is required for termination of Toll-like receptor responses," *Nat. Immunol.* 5:1052-1060,2004.
Durkop et al., "Differential expression and function of A20 and TRAF1 in Hodgkin lymphoma and anaplastic large cell lymphoma and their induction by CD30 stimulation," *J. Path.*, 200:229-239, 2003.
Ferretti et al., "PReMod: a database of genome-wide mammalian cis-regulatory module predictions," *Nucleic Acids Res.*, 35:D122-D126, 2007.
Fung et al., "Analysis of 17 autoimmune disease-associated variants in type 1 diabetes identifies 6q23/TNFAIP3 as a susceptibility locus," *Genes and Immunity*, 1-4, 2008.
Gaffney et al., "Fine-mapping chromosome 20 in 230 systemic lupus erythematosus sib pair and multiplex families: evidence for genetic epistasis with chromosome 16q12," *Am. J. Hum. Genet.*, 78:747-758, 2006.
Gaffney et al., "A genome-wide search for susceptibility genes in human systemic lupus erythematosus sib-pair families," *PNAS*, 95:14875-14879, 1998.
Gaffney, "Genome screening in human systemic lupus erythematosus: results from a second Minnesota cohort and combined analyses of 187 sib-pair families," *Am. J. Hum. Genet.*, 66:547-556, 2000.
Graham et al., "Genetic variants near TNFAIP3 on 6q23 are associated with systemic lupus erythematosus," *Nature Genetics*, 40:1059-1061, 2008.
Grey et al., "Adenovirus-mediated gene transfer of A20 in murine islets inhibits Fas-induced apoptosis," *Transplant Proc.*, 33:577-578, 2001.
Grey et al., "Genetic engineering of a suboptimal islet graft with A20 preserves beta cell mass and function," *J. Immunol.*, 170:6250-6256,2003.
Harley et al., "The genetics of human systemic lupus erythematosus," *Current Opinions in Immunology*, 10:690-696, 1998.
He and Ting, "A20 inhibits tumor necrosis factor (TNF) alpha-induced apoptosis by disrupting recruitment of TRADD and RIP to the TNF receptor 1 complex in Jurkat T cells," *Mol. Cell Biol.*, 22:3034-3045, 2002.
Heyninck and Beyaert, "The cytokine-inducible zinc finger protein A20 inhibits IL-1-induced NF-kappaB activation at the level of TRAF6," *FEBS Lett.*, 442:147-150, 1999.
Heyninck and Beyaert, "A20 inhibits NF-kappaB activation by dual ubiquitin-editing functions," *Trends Biochem. Sci.*, 30:1-4, 2005.
Heyninck, "The zinc finger protein A20 inhibits TNF-induced NF-kappaB-dependent gene expression by interfering with an RIP- or TRAF2-mediated transactivation signal and directly binds to a novel NF-kappaB-inhibiting protein ABIN," *J. Cell Biol.*, 145:1471-1482, 1999. Jarvis et al., "Human cytomegalovirus attenuates interleukin-1 beta and tumor necrosis factor alpha proinflammatory signaling by inhibition of NF-kappaB activation," *J. Virol.*, 80:5588-5598, 2006.
Liuwantara et al., "Nuclear factor-kappaB regulates beta-cell death: a critical role for A20 in beta-cell protection," *Diabetes*, 55:2491-2501, 2006.
Moser et al., "Genome scan of human systemic lupus erythematosus: evidence for linkage on chromosome 1q in African-American pedigrees," *PNAS*, 95:14869-14874, 1998.
Musone et al., "Multiple polymorphisms in the TNFAIP3 region are independently associated with systemic lupus erythematosus," *Nat. Genet.*, 40:1062-1064, 2008.
NCBI Accession No. NM_006290.2, *Homo sapiens* tumor necrosis factor, alpha-induced protein 3 (TNFAIP3), mRNA, 1990.
NCBI Accession No. NP_006281.1, Tumor necrosis factor, alpha-induced protein 3 [*Homo Sapiens*], 1990.
Plenge et al., "Two independent alleles at 6q23 associated with risk of rheumatoid arthritis," *Nature Genetics*, 39:1477-1482, 2007.

(Continued)

*Primary Examiner* — Katherine Salmon
(74) *Attorney, Agent, or Firm* — Fulbright & Jaworski

(57) ABSTRACT

The present invention provides methods for the prediction and diagnosis of autoimmune diseases, including Systemic Lupus Erythematosus, using single nucleotide polymorphism in TNFAIP3 (A20).

13 Claims, 12 Drawing Sheets

OTHER PUBLICATIONS

Ramensky et al., "Human non-synonymous SNPs: server and survey," *Nucleic Acid Res.*, 30:3894-3900, 2002.

Song et al., "The tumor necrosis factor-inducible zinc finger protein A20 interacts with TRAF1/TRAF2 and inhibits NF-kappaB activation," *PNAS*, 93:6721-6725, 1996.

Thomson et al., "Rheumatoid arthritis association at 6q23," *Nature Genetics*, 39:1431-1433, 2007.

Wellcome Trust Case Control Consortium, "Genome-wide association study of 14,000 cases of seven common disease and 3,000 shared controls," *Nature*, 447:661-678, 2007.

Wertz et al., "De-ubiquitination and ubiquitin ligase domains of A20 downregulate NF-kappaB signalling," *Nature*, 430:694-699, 2004.

Idel et al., "A20, a regulator of NFκB, maps to an atherosclerosis locus and differs between parental sensitive C577BL/6J and resistant FVB/N strains," *PNAS*, 100:14235-14240, 2003.

Boonyasrisawat et al., "Tag polymorphisms at the A20 (TNFAIP3) locus are associated with lower gene expression and increased risk of coronary artery disease in type 2 diabetes," *Diabetes*, 56:499-505, 2007.

Gaffney et al., "Recent advances in the genetics of systemic lupus erythematosus," *Rheumatic Disease Clinics of North America*, 28:111-126, 2002.

Graham et al., "A genome-wide association scan identifies tumor necrosis factor alpha inducible protein 3 (TNFAIP3/A20) as a susceptibility locus for systemic lupus erythematosus," *Arthritis & Rheumatism*, 58 (Suppl. S.):S621-S622, Abstract # 1218, 2008.

Idel et al., "A20, a regulator of NFκB, maps to an atherosclerosis locus and differs between parental sensitive C577BL/6J and resistant FVB/N strains," *PNAS*, 100:14235-14240, 2003.

Kyogoku et al., "Genetic association if the R620W polymorphism of protein tyrosine phosphate PTPN22 with human SLE," *Am. J. Hum. Genet.*, 75:504-507, 2004.

Lessard et al., "Imputation and meta-analysis define a similar to 100 kb risk haplotype spanning TNFAIP3 associated with SLE," *Arthritis & Rheumatism*, 58 (Suppl. S): S219, Abstract # 140, 2008.

Luettich et al., "Global gene expression analysis identifies a novel apoptotic pathway in cutaneous lupus erythematosus," *J. Invest. Dermat.*, vol. 121, Abstract # 0113, 2003.

Musone et al., "Multiple polymorphisms in the TNFAIP3 region are independently associated with systemic lupus erythematosus," *Arthritis & Rheumatism*, 58 (Suppl. S):S622, Abstract # 1219, 2008.

\* cited by examiner

Fig. 1A-B

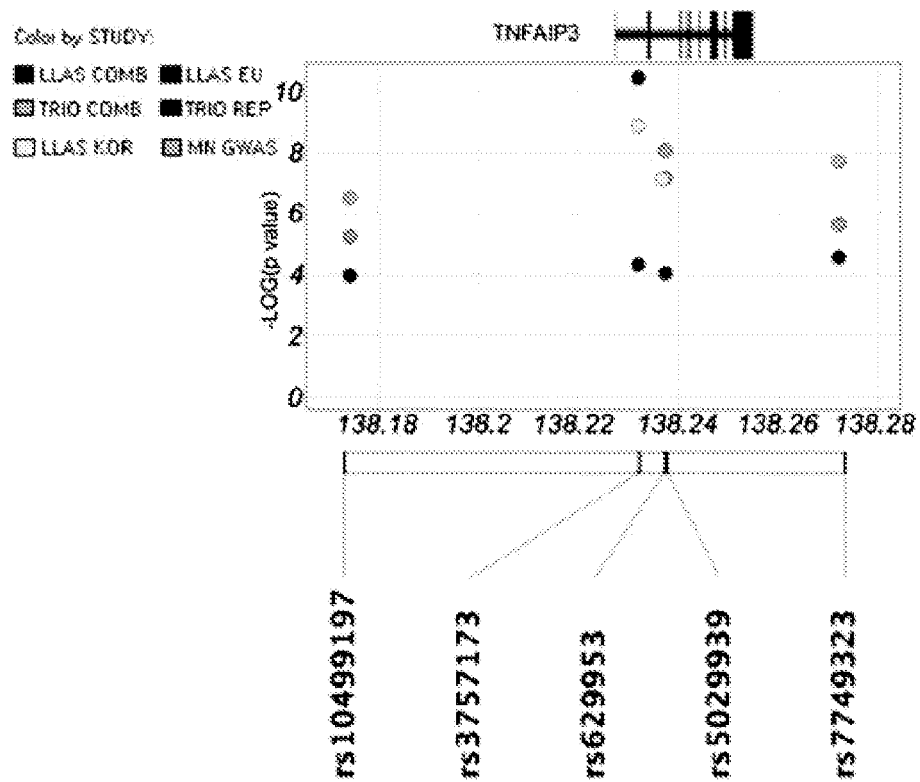
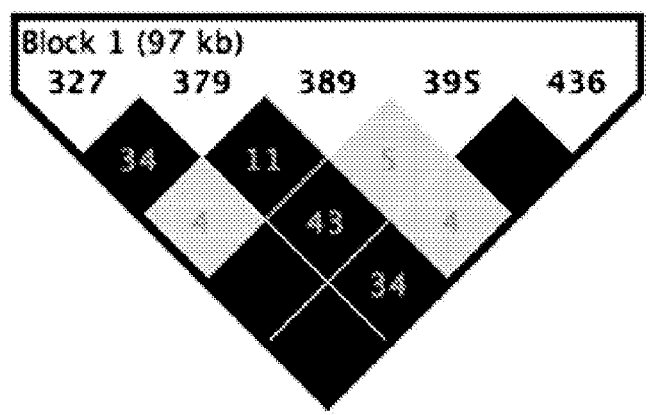
Fig. 4

PREDICTING AND DIAGNOSING PATIENTS WITH AUTOIMMUNE DISEASE

This application claims benefit of priority to U.S. Provisional Application Ser. No. 60/988,675, filed Nov. 16, 2007, the entire contents of which are hereby incorporated by reference.

This invention was made with grant support under grant no. AI063274 from the National Institutes of Health—National Institutes of Allergy and Infectious Disease. The government has certain rights in the invention.

BACKGROUND OF THE INVENTION

A. Field of the Invention

The present invention relates to the fields of molecular biology, pathology and genetics. More specifically, the invention relates to methods of predicting and diagnosing autoimmune disease based on the presence or absence of single nucleotide polymorphisms.

B. Related Art

Autoimmune diseases comprises a large number of widely varying illnesses. Their common feature is the existence of an immune response in the subject against one or more "self" antigens, including such wide ranging molecules as proteins, DNA and carbohydrates. These diseases can cause symptoms ranging from only mild discomfort to the patient, to complete debilitation and death. Most of autoimmune diseases remain very enigmatic, not only in their molecular basis and precipitating factors, but in their prediction, progression and treatment. As such, they continue to provide a considerable challenge to the healthcare industry.

Most genetic-based diseases do not generally have a simple, single genetic cause. Moreover, they are usually affected by environmental factors as well. The same can be said for autoimmune diseases, where defects in multiple genes often are involved. The situation is not aided by clinical diagnosis, since (a) familial autoimmune disease is often characterized by related individuals suffering from distinct autoimmune defects, and (b) the same autoimmune disease may manifest itself differently in different individuals at different times. Thus, one is left with a difficult, if not impossible, clinical diagnosis even when some genetic information is available. That is why researches continue to seek out better and more complete genetic bases for autoimmune diseases.

Systemic Lupus Erythematosus (SLE), like other autoimmune diseases, is mediated by a complex interaction of genetic and environmental elements. The genetic component of this interaction is clearly important: 20% of people with SLE have a relative who has or will have SLE. It is commonly believed that environmental factors may trigger a genetic predisposition to such diseases. Although the crucial role of genetic predisposition in susceptibility to SLE has been known for decades, only minimal progress has been made towards elucidating the specific genes involved in human disease. It is also suspected that SLE may be related to genetic defects in apoptosis. For example, mice lacking the gene for DNase1 develop SLE by 6 to 8 months of age.

Family studies have identified a number of genetic regions associated with elevated risk for SLE, although no specific genes have yet been identified. Harley et al. (1998); Wakeland et al. (2001). For example, 1q42 has been linked to SLE in three independent studies. Reviewed in Gaffney et al. (1998). Other genetic locations revealed by model-based linkage analysis include 1q23 and 11q14 in African Americans, 14q11, 4p15, 11q25, 2q32, 19q13, 6q26-27, and 12p12-11 in European Americans, with 1q23, 13q32, 20q13, and 1q31 showing up in combined pedigrees. Moser et al. (1998). Associations have also been shown for the genetic markers HLA-DR2 and HLA-DR3. Arnett et al. (1992). More recently, expression profiling of peripheral blood mononuclear cells of SLE patients using microarrays has shown that about half of the patients demonstrate disregulated expression of genes in the IFN pathway. Baechler et al. (2003).

Despite these important observations, it is far from clear that one can predict the existence or predisposition to SLE based on this handful of genetic information. In all likelihood, a much more robust analysis using more and better genetic markers to identify SLE (and distinguish it from other autoimmune diseases) will be required.

SUMMARY OF THE INVENTION

Thus, in accordance with the present invention, there is provided a method of identifying a subject afflicted with or at risk of developing an autoimmune disease comprising (a) obtaining a nucleic acid-containing sample from said subject; (b) determining the presence or absence of a single nucleotide polymorphism (SNP) in TNFAIP3, wherein the presence of a SNP in TNFAIP3 associated with increased risk of an autoimmune disease indicates that said subject is afflicted with or at risk of developing an autoimmune disease. The method may further comprise determining the presence or absence of a second, a third, a fourth, a fifth or all six SNPs from TNFAIP3. The SNPs may be rs10499197, rs3757173, rs629953, rs5029939, rs2230926 and/or rs7749323. The method may further comprise taking a clinical history from said subject. The sample may be blood, sputum, saliva, mucosal scraping or tissue biopsy.

The autoimmune disease is systemic lupus erythematosus, but may also be Sjogren's syndrome, rheumatoid arthritis, juvenile onset diabetes mellitus, Wegener's granulomatosis, inflammatory bowel disease, polymyositis, dermatomyositis, multiple endocrine failure, Schmidt's syndrome, autoimmune uveitis, Addison's disease, adrenalitis, Graves' disease, thyroiditis, Hashimoto's thyroiditis, autoimmune thyroid disease, pernicious anemia, gastric atrophy, chronic hepatitis, lupoid hepatitis, atherosclerosis, presenile dementia, demyelinating diseases, multiple sclerosis, subacute cutaneous lupus erythematosus, hypoparathyroidism, Dressler's syndrome, myasthenia gravis, autoimmune thrombocytopenia, idiopathic thrombocytopenic purpura, hemolytic anemia, pemphigus vulgaris, pemphigus, dermatitis herpetiformis, alopecia arcata, pemphigoid, scleroderma, progressive systemic sclerosis, CREST syndrome (calcinosis, Raynaud's phenomenon, esophageal dysmotility, sclerodactyly, and telangiectasia), adult onset diabetes mellitus (Type II diabetes), male and female autoimmune infertility, ankylosing spondolytis, ulcerative colitis, Crohn's disease, mixed connective tissue disease, polyarteritis nedosa, systemic necrotizing vasculitis, juvenile onset rheumatoid arthritis, glomerulonephritis, atopic dermatitis, atopic rhinitis, Goodpasture's syndrome, Chagas' disease, sarcoidosis, rheumatic fever, asthma, recurrent abortion, anti-phospholipid syndrome, farmer's lung, erythema multiforme, post cardiotomy syndrome, Cushing's syndrome, autoimmune chronic active hepatitis, bird-fancier's lung, allergic disease, allergic encephalomyelitis, toxic epidermal necrolysis, alopecia, Alport's syndrome, alveolitis, allergic alveolitis, fibrosing alveolitis, interstitial lung disease, erythema nodosum, pyoderma gangrenosum, transfusion reaction, leprosy, malaria, leishmaniasis, trypanosomiasis, Takayasu's arteritis, polymyalgia rheumatica, temporal arteritis, schistosomiasis, giant cell arteritis, ascariasis, aspergillosis, Sampter's syndrome, eczema, lymphomatoid granulomatosis, Behcet's disease, Caplan's syndrome, Kawasaki's disease, dengue, encephalomyelitis, endocarditis, endomyocardial fibrosis, endophthalmitis, erythema elevatum et diutinum, psoriasis, erythroblastosis fetalis, eosinophilic faciitis, Shulman's syndrome, Felty's syndrome, filariasis, cyclitis, chronic cyclitis, heterochronic cyclitis, Fuch's cyclitis, IgA nephropathy, Henoch-Schonlein purpura, glomerulonephritis, graft versus host disease, transplantation rejection, human immunodeficiency virus infection, echovirus infection, cardiomyopathy, Alzheimer's disease, parvovirus infection, rubella virus infection, post vaccination syndromes, congenital rubella infection, Hodgkin's and Non-Hodgkin's lymphoma, renal cell carcinoma, multiple myeloma, Eaton-Lambert syndrome, relapsing polychondritis, malignant melanoma, cryoglobulinemia, Waldenstrom's macroglobulemia, Epstein-Barr virus infection, mumps, Evan's syndrome, and autoimmune gonadal failure.

The method may also further comprise treating said subject based on the results of step (b). Determining may comprise nucleic acid amplification, such as PCR, primer extension, restriction digestion, sequencing, SNP specific oligonucleotide hybridization, or DNAse protection. Determining may also comprise assessing the presence or absence of a genetic marker that is in linkage disequilibrium with one or more of rs10499197, rs3757173, rs629953, rs5029939, rs2230926 and rs7749323.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one."

It is contemplated that any embodiment discussed in this specification can be implemented with respect to any method or composition of the invention, and vice versa. Furthermore, compositions and kits of the invention can be used to achieve methods of the invention.

Throughout this application, the term "about" is used to indicate that a value includes the inherent variation of error for the device, the method being employed to determine the value, or the variation that exists among the study subjects.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 4. LD relationships between the most associated markers in TNFAIP3. Scatterplot is the same as in FIG. 1 except only the selected markers are represented. LD relationships are shown on the Haploview image. Correlation coefficient $r^2$ is shown in each of the squares. The alleles for the various haplotypes are depicted at the bottom. The arrow points to the rare haplotype from which the association with SLE emanates. The alleles in red are most correlated ($r^2 > 0.79$).

(FIG. 5A). Results showing full 5 MB imputation interval. Imputed SNPs are shown as triangles and observed SNPs are shown as diamonds. Locations of genes within the interval are located at the top of the panel. (FIG. 5B) Expanded view of region surrounding TNFAIP3. Eleven imputed SNPs demonstrate association with SLE (triangles). Associated observed SNPs, rs10499197, rs5029939, and rs7749323 are shown as diamonds.

(FIG. 8A) PCR of cDNA from EBV-transformed B cells lines was performed with five primers spanning the entire gene product. (FIG. 8B) Predicted splice products as shown in the diagram were detected. No alternative products were detected. Data is representative of two experiments.

(FIG. 9A) EBV cell lines (WT, Het, Hom risk) were stimulated with and without LPS or PMA/Ionomycin. Cells were harvested six hours later and TNFAIP3 mRNA expression was measured by real-time PCR using TaqMan chemistry. Data shown are the average of two independent cell lines of each genotype. (FIG. 9B) WT and homozygous risk cell lines were stimulated with and without LPS 10 ng/ml and cells were harvested at 6 and 14 hours post LPS. Western blotting was performed using A20 and GAPDH specific antibodies. The ratio of A20 versus GAPDH density is shown. (FIG. 9C) Intracellular TNFα staining in PMA/Ionomycin and LPS stimulated EBV-transformed B cell lines expressing WT or homozygous risk haplotypes. Cells were stimulated for 14 hours, fixed and permeabilized before staining with PE-anti-TNFα or control PE-IgG antibodies. Intracellular fluorescence was detected by flow cytometry. The percentage of TNFα positive cells within the area R2 gate is shown. (FIG. 9D) EBV cell lines (N=2) carrying WT, Het or homozygous risk haplotypes were cultured overnight in serum free medium. Media from unstimulated cells was removed and analyzed for cytokine/chemokine content using Luminex Bead assay.

DETAILED DESCRIPTION OF THE INVENTION

I. The Present Invention

The present invention involves the identification of multiple SNPs in the gene for TNFAIP3 (A20) that are shown to correlate with SLE and thus can be used both diagnostically and prognostically. The invention is described in detail below.

II. TNFAIP3

A20

Specific pathways to negatively regulate NF-κB activation downstream of TNF and TLR are not well understood. Perhaps the best-characterized mechanism for regulating NF-κB is mediated by the ubiquitin modifying protein, TNFAIP3, also known as A20 (Heyninck and Beyaert, 1999; Heyninck, 1999; Heyninck and Beyaert, 2005). TNFAIP3 is a zinc-finger protein whose gene, tnfaip3 (tumor necrosis factor, alpha-induced protein 3), is rapidly increased in response to TNF-family receptor signals, including TNFα, IL-1 and CD40 ligand, as well as toll-like receptor (TLR) signals like LPS, CpG, and peptidoglycan (reviewed in (Beyaert et al., 2000)). TNFAIP3 is present in myeloid cells including monocytes, macrophages, and dendritic cells as well as lymphoid cells including T and B cells and NK cells. TNFAIP3 is also induced by TLR and TNFα stimulation in many non-hematopoietic cells including endothelial cells and fibroblasts.

Figure 1:
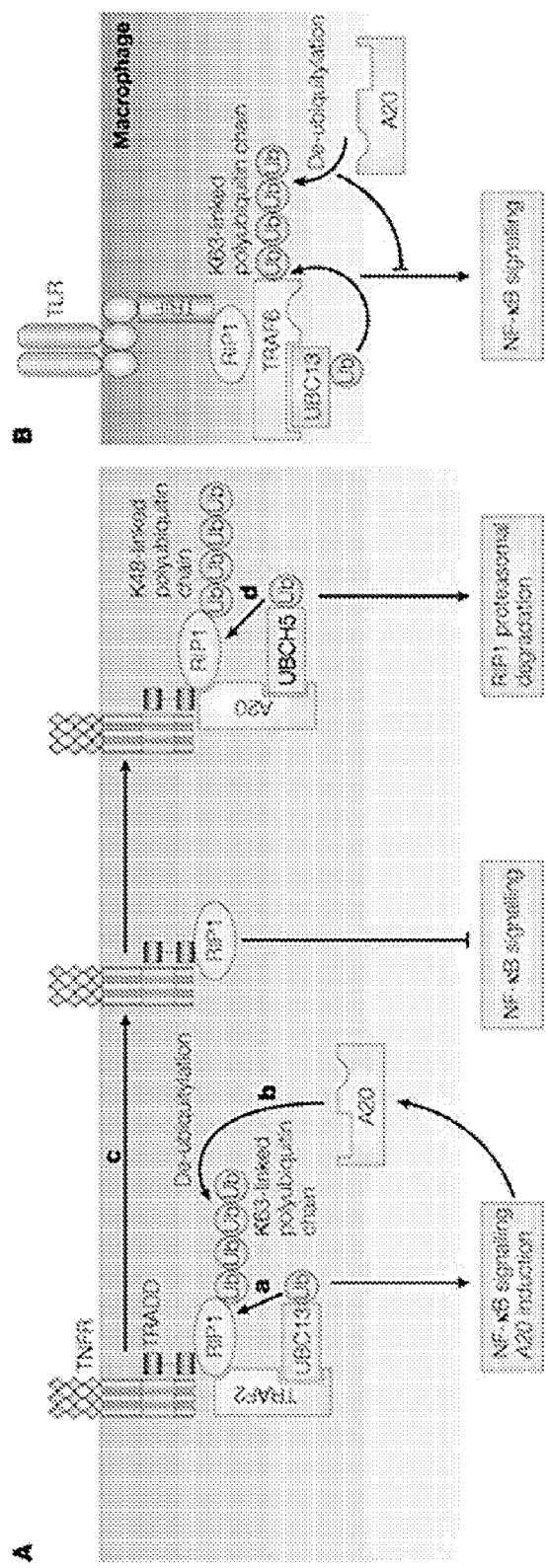
FIGS. 1A-1B. A20 functions both to de-ubiquinate K63 linked polyubiquitin on RIP1 or TRAF6 that results from stimulation via TNF or TLR receptors, respectively. A20 then catalyzes the ubiquination at K48 which targets the respective mediators for proteosomal degradation.

TNFAIP3 is a 775 amino acid protein with a N-terminal ovarian tumor (OTU) domain and seven repeating zinc fingers in the C-terminus. TNFAIP3 functions as an ubiquitin-editing enzyme with de-ubiquitinating activity in the OTU domain and E3 ubiquitin ligase activities in the fourth zinc finger domain (reviewed in (Heyninck and Beyaert et al., 2005)). This dual function of TNFAIP3 is critical for its ability to negatively regulate NF-κB. For example, after TNFα stimulation resulting in NF-κB activation, TNFAIP3 is induced and recruited to TNFR-1 complex. TNFAIP3 then associates with receptor interacting protein (RIP), a critical regulator of NF-κB. TNFAIP3 removes the protective lysine-63-linked polyubiquitin chain from RIP and subsequently conjugates a lysine-48-linked polyubiquitin chain to RIP thereby sending it to the proteosome for degradation resulting in termination of NF-κB signaling (Heyninck and Beyaert et al., 1999; Wertz et al., 2004) (FIG. 1). TNFAIP3 further regulates NF-κB activation by modifying the ubiquitin status of several other upstream proteins including TRAF1, TRAF2, and TRADD (Song et al., 1996; He and Ting, 2002). TNFAIP3 serves a similar role in modifying TRAF6, a key regulator of IL-1 and TLR signals (Heyninck and Beyaert, 1999).

TNFAIP3 is one of several anti-apoptotic genes that are induced upon NF-κB activation or by reactive oxygen species and plays a vital cytoprotective role (Baichwal and Baeuerle, 1997). TNFAIP3 inhibits TNFα induced cell death by interacting with and modifying TNFR-1 associated death domain protein (TRADD) and RIP (Heyninck, 1999; He and Ting 2002). Recent studies have shown that expression of TNFAIP3 provides an anti-apoptotic signal after NF-κB stimulation in a variety of cells including beta cells (Liuwantara et al., 2006). Islets from NOD mice fail to induce TNFAIP3 upon TNFα stimulation leading to enhanced beta cell death (Grey et al., 1999; Liuwantara et al., 2006); while overexpression of TNFAIP3 in transplanted islets leads to substantially improved transplant survival (Grey et al., 2001; Grey et al., 2003). Not surprisingly, TNFAIP3 is highly expressed in some tumors including nodular lymphocyte-predominant Hodgkin's lymphoma and anaplastic diffuse large B cell lymphoma (Durkop et al., 2003).

TNFAIP3 deficient (A20−/−) mice develop severe spontaneous inflammation of the bowels, skins, kidneys, liver, and joints and die prematurely by 6 weeks of age. Cells from these mice display multiple defects in regulating TNF signals with sustained NF-κB activation and cellular resistance to programmed cell death (Lee et al., 2000). These observations highlight A20's critical roles in terminating TNF responses in vivo. Subsequent studies in mice doubly deficient in TNFAIP3 and TNFR-1 or TNFAIP3 and TNF revealed that TNFAIP3 is required to terminate TLR signals in vivo independent of TNF responses (Boone et al., 2004). Thus TNFAIP3 is needed to negatively regulate a variety of innate stimuli and protect the host from excessive or prolonged immune responses.

The role of TNFAIP3 in autoimmune disease in humans remains to be defined at this time and is the focus of this grant proposal. One enticing study using microarray data of neutrophils of children with polyarticular juvenile rheumatoid arthritis (JRA) reveals a 4.5-fold decrease in TNFAIP3 expression compared to neutrophils from healthy children (Jarvis et al., 2006). This data coupled, with the inventors' convincing preliminary genetic results suggest that changes in TNFAIP3 expression or function may be a risk for autoimmune disease.

As discussed below, the present inventors have identified at least five distinct SNPs within the TNFAIP3 gene that have a significant statistical correlation with SLE. The inventors propose that by examining these SNPs, it is possible identify those subjects with SLE, as well as those at risk of developing SLE and other autoimmune diseases. The accession number for the DNA sequence is NM_006290.2 (coding 76-2439) (SEQ ID NO:1) and the protein sequence is NP_006281.1 (SEQ ID NO:2), both of which are incorporated by reference.

III. SNP-Based Diagnostics

Knowledge of DNA polymorphisms can prove very useful in a variety of applications, including diagnosis and treatment of autoimmune disease. A particular kind of polymorphism, called a single nucleotide polymorphism, or SNP (pronounced "snip"), is a small genetic change or variation that can occur within a person's DNA sequence. The genetic code is specified by the four nucleotide "letters" A (adenine), C (cytosine), T (thymine), and G (guanine). SNP variation occurs when a single nucleotide, such as an A, replaces one of the other three nucleotide letters—C, G, or T.

An example of a SNP is the alteration of the DNA segment AAGGTTA to ATGGTTA, where the second "A" in the first snippet is replaced with a "T." On average, SNPs occur in the human population more than 1 percent of the time. Because only about 3 to 5 percent of a person's DNA sequence codes for the production of proteins, most SNPs are found outside of "coding sequences." SNPs found within a coding sequence are of particular interest to researchers because they are more likely to alter the biological function of a protein. Because of the recent advances in technology, coupled with the unique ability of these genetic variations to facilitate gene identification, there has been a recent flurry of SNP discovery and detection.

Finding single nucleotide changes in the human genome seems like a daunting prospect, but over the last 20 years, biomedical researchers have developed a number of techniques that make it possible to do just that. Each technique uses a different method to compare selected regions of a DNA sequence obtained from multiple individuals who share a common trait. In each test, the result shows a physical difference in the DNA samples only when a SNP is detected in one individual and not in the other.

Many common diseases in humans are not caused by a genetic variation within a single gene, but instead are influenced by complex interactions among multiple genes as well as environmental and lifestyle factors. Although both environmental and lifestyle factors add tremendously to the uncertainty of developing a disease, it is currently difficult to measure and evaluate their overall effect on a disease process. Therefore, when looking at SNPs, one refers mainly to a person's genetic predisposition, or the potential of an individual to develop a disease based on genes and hereditary factors. This is particularly true in diagnosis of autoimmune disease.

Each person's genetic material contains a unique SNP pattern that is made up of many different genetic variations. Researchers have found that most SNPs are not responsible for a disease state. Instead, they serve as biological markers for pinpointing a disease on the human genome map, because they are usually located near a gene found to be associated with a certain disease. Occasionally, a SNP may actually cause a disease and, therefore, can be used to search for and isolate the disease-causing gene.

To create a genetic test that will screen for an autoimmune disease, one will collect blood or tissue samples from a group of individuals affected by the disease and analyze their DNA for SNP patterns. One then compares these patterns to patterns obtained by analyzing the DNA from a group of individuals unaffected by the disease. This type of comparison, called an "association study," can detect differences between the SNP patterns of the two groups, thereby indicating which pattern is most likely associated with the disease-causing gene. Eventually, SNP profiles that are characteristic of a variety of diseases will be established. These profiles can then be applied to the population at general, or those deemed to be at particular risk of developing an autoimmune disease.

A. Methods of Assaying for SNPs

There are a large variety of techniques that can be used to assess SNPs, and more are being discovered each day. The following is a very general discussion of a few of these techniques that can be used in accordance with the present invention.

1. RFLP

Restriction Fragment Length Polymorphism (RFLP) is a technique in which different DNA sequences may be differentiated by analysis of patterns derived from cleavage of that DNA. If two sequences differ in the distance between sites of cleavage of a particular restriction endonuclease, the length of the fragments produced will differ when the DNA is digested with a restriction enzyme. The similarity of the patterns generated can be used to differentiate species (and even strains) from one another.

Restriction endonucleases in turn are the enzymes that cleave DNA molecules at specific nucleotide sequences depending on the particular enzyme used. Enzyme recognition sites are usually 4 to 6 base pairs in length. Generally, the shorter the recognition sequence, the greater the number of fragments generated. If molecules differ in nucleotide sequence, fragments of different sizes may be generated. The fragments can be separated by gel electrophoresis. Restriction enzymes are isolated from a wide variety of bacterial genera and are thought to be part of the cell's defenses against invading bacterial viruses. Use of RFLP and restriction endonucleases in SNP analysis requires that the SNP affect cleavage of at least one restriction enzyme site.

2. Primer Extension

The primer and no more than three NTPs may be combined with a polymerase and the target sequence, which serves as a template for amplification. By using less than all four NTPs, it is possible to omit one or more of the polymorphic nucleotides needed for incorporation at the polymorphic site. It is important for the practice of the present invention that the amplification be designed such that the omitted nucleotide(s) is (are) not required between the 3' end of the primer and the target polymorphism. The primer is then extended by a nucleic acid polymerase, in a preferred embodiment by Taq polymerase. If the omitted NTP is required at the polymorphic site, the primer is extended up to the polymorphic site, at which point the polymerization ceases. However, if the omitted NTP is not required at the polymorphic site, the primer will be extended beyond the polymorphic site, creating a longer product. Detection of the extension products is based on, for example, separation by size/length which will thereby reveal which polymorphism is present.

A specific form of primer extension can be found in U.S. Ser. No. 10/407,846, which is hereby specifically incorporated by reference.

3. Oligonucleotide Hybridization

Oligonucleotides may be designed to hybridize directly to a target site of interest. The most common form of such analysis is where oligonucleotides are arrayed on a chip or plate in a "microarray." Microarrays comprise a plurality of oligos spatially distributed over, and stably associated with, the surface of a substantially planar substrate, e.g., biochips. Microarrays of oligonucleotides have been developed and find use in a variety of applications, such as screening and DNA sequencing.

In gene analysis with microarrays, an array of "probe" oligonucleotides is contacted with a nucleic acid sample of interest, i.e., target. Contact is carried out under hybridization conditions and unbound nucleic acid is then removed. The resultant pattern of hybridized nucleic acid provides information regarding the genetic profile of the sample tested. Methodologies of gene analysis on microarrays are capable of providing both qualitative and quantitative information.

A variety of different arrays which may be used are known in the art. The probe molecules of the arrays which are capable of sequence specific hybridization with target nucleic acid may be polynucleotides or hybridizing analogues or mimetics thereof, including: nucleic acids in which the phosphodiester linkage has been replaced with a substitute linkage, such as phosphorothioate, methylimino, methylphosphonate, phosphoramidate, guanidine and the like; nucleic acids in which the ribose subunit has been substituted, e.g., hexose phosphodiester; peptide nucleic acids; and the like. The length of the probes will generally range from 10 to 1000 nts, where in some embodiments the probes will be oligonucleotides and usually range from 15 to 150 nts and more usually from 15 to 100 nts in length, and in other embodiments the probes will be longer, usually ranging in length from 150 to 1000 nts, where the polynucleotide probes may be single- or double-stranded, usually single-stranded, and may be PCR fragments amplified from cDNA.

The probe molecules on the surface of the substrates will correspond to selected genes being analyzed and be positioned on the array at a known location so that positive hybridization events may be correlated to expression of a particular gene in the physiological source from which the target nucleic acid sample is derived. The substrates with which the probe molecules are stably associated may be fabricated from a variety of materials, including plastics, ceramics, metals, gels, membranes, glasses, and the like. The arrays may be produced according to any convenient methodology, such as preforming the probes and then stably associating them with the surface of the support or growing the probes directly on the support. A number of different array configurations and methods for their production are known to those of skill in the art and disclosed in U.S. Pat. Nos. 5,445,934, 5,532,128, 5,556,752, 5,242,974, 5,384,261, 5,405,783, 5,412,087, 5,424,186, 5,429,807, 5,436,327, 5,472,672, 5,527,681, 5,529,756, 5,545,531, 5,554,501, 5,561,071, 5,571,639, 5,593,839, 5,599,695, 5,624,711, 5,658,734, 5,700,637, and 6,004,755.

Following hybridization, where non-hybridized labeled nucleic acid is capable of emitting a signal during the detection step, a washing step is employed where unhybridized labeled nucleic acid is removed from the support surface, generating a pattern of hybridized nucleic acid on the substrate surface. A variety of wash solutions and protocols for their use are known to those of skill in the art and may be used.

Where the label on the target nucleic acid is not directly detectable, one then contacts the array, now comprising bound target, with the other member(s) of the signal producing system that is being employed. For example, where the label on the target is biotin, one then contacts the array with streptavidin-fluorescer conjugate under conditions sufficient for binding between the specific binding member pairs to occur. Following contact, any unbound members of the signal producing system will then be removed, e.g., by washing. The specific wash conditions employed will necessarily depend on the specific nature of the signal producing system that is employed, and will be known to those of skill in the art familiar with the particular signal producing system employed.

The resultant hybridization pattern(s) of labeled nucleic acids may be visualized or detected in a variety of ways, with the particular manner of detection being chosen based on the particular label of the nucleic acid, where representative detection means include scintillation counting, autoradiography, fluorescence measurement, calorimetric measurement, light emission measurement and the like.

Prior to detection or visualization, where one desires to reduce the potential for a mismatch hybridization event to generate a false positive signal on the pattern, the array of hybridized target/probe complexes may be treated with an endonuclease under conditions sufficient such that the endonuclease degrades single stranded, but not double stranded DNA. A variety of different endonucleases are known and may be used, where such nucleases include: mung bean nuclease, S1 nuclease, and the like. Where such treatment is employed in an assay in which the target nucleic acids are not labeled with a directly detectable label, e.g., in an assay with biotinylated target nucleic acids, the endonuclease treatment will generally be performed prior to contact of the array with the other member(s) of the signal producing system, e.g., fluorescent-streptavidin conjugate. Endonuclease treatment, as described above, ensures that only end-labeled target/probe complexes having a substantially complete hybridization at the 3' end of the probe are detected in the hybridization pattern.

Following hybridization and any washing step(s) and/or subsequent treatments, as described above, the resultant hybridization pattern is detected. In detecting or visualizing the hybridization pattern, the intensity or signal value of the label will be not only be detected but quantified, by which is meant that the signal from each spot of the hybridization will be measured and compared to a unit value corresponding the signal emitted by known number of end-labeled target nucleic acids to obtain a count or absolute value of the copy number of each end-labeled target that is hybridized to a particular spot on the array in the hybridization pattern.

4. Amplification of Nucleic Acids

In a particular embodiment, it may be desirable to amplify the target sequence before evaluating the SNP. Nucleic acids used as a template for amplification may be isolated from cells, tissues or other samples according to standard methodologies (Sambrook et al., 1989). In certain embodiments, analysis is performed on whole cell or tissue homogenates or biological fluid samples without substantial purification of the template nucleic acid. The nucleic acid may be genomic DNA or fractionated or whole cell RNA. Where RNA is used, it may be desired to first convert the RNA to a complementary DNA. The DNA also may be from a cloned source or synthesized in vitro.

The term "primer," as used herein, is meant to encompass any nucleic acid that is capable of priming the synthesis of a nascent nucleic acid in a template-dependent process. Typically, primers are oligonucleotides from ten to twenty or thirty base pairs in length, but longer sequences can be employed. Primers may be provided in double-stranded or single-stranded form, although the single-stranded form is preferred.

Pairs of primers designed to selectively hybridize to nucleic acids flanking the polymorphic site are contacted with the template nucleic acid under conditions that permit selective hybridization. Depending upon the desired application, high stringency hybridization conditions may be selected that will only allow hybridization to sequences that are completely complementary to the primers. In other embodiments, hybridization may occur under reduced stringency to allow for amplification of nucleic acids containing one or more mismatches with the primer sequences. Once hybridized, the template-primer complex is contacted with one or more enzymes that facilitate template-dependent nucleic acid synthesis. Multiple rounds of amplification, also referred to as "cycles," are conducted until a sufficient amount of amplification product is produced.

It is also possible that multiple target sequences will be amplified in a single reaction. Primers designed to expand specific sequences located in different regions of the target genome, thereby identifying different polymorphisms, would be mixed together in a single reaction mixture. The resulting amplification mixture would contain multiple amplified regions, and could be used as the source template for polymorphism detection using the methods described in this application.

A number of template dependent processes are available to amplify the oligonucleotide sequences present in a given template sample. One of the best known amplification methods is the polymerase chain reaction (referred to as PCR™), which is described in detail in U.S. Pat. Nos. 4,683,195, 4,683,202 and 4,800,159, and in Innis et al., 1988, each of which is incorporated herein by reference in their entirety.

A reverse transcriptase PCR™ amplification procedure may be performed when the source of nucleic acid is fractionated or whole cell RNA. Methods of reverse transcribing RNA into cDNA are well known (see Sambrook et al., 1989).

Alternative methods for reverse polymerization utilize thermostable DNA polymerases. These methods are described in WO 90/07641. Polymerase chain reaction methodologies are well known in the art. Representative methods of RT-PCR are described in U.S. Pat. No. 5,882,864.

Another method for amplification is ligase chain reaction ("LCR"), disclosed in European Application No. 320 308, incorporated herein by reference in its entirety. U.S. Pat. No. 4,883,750 describes a method similar to LCR for binding probe pairs to a target sequence. A method based on PCR and oligonucleotide ligase assay (OLA), disclosed in U.S. Pat. No. 5,912,148, may also be used.

Another ligase-mediated reaction is disclosed by Guilfoyle et al. (1997). Genomic DNA is digested with a restriction enzyme and universal linkers are then ligated onto the restriction fragments. Primers to the universal linker sequence are then used in PCR to amplify the restriction fragments. By varying the conditions of the PCR, one can specifically amplify fragments of a certain size (i.e., less than a 1000 bases). An example for use with the present invention would be to digest genomic DNA with XbaI, and ligate on M13-universal primers with an XbaI over hang, followed by amplification of the genomic DNA with an M13 universal primer. Only a small percentage of the total DNA would be amplified (the restriction fragments that were less than 1000 bases). One would then use labeled primers that correspond to a SNP are located within XbaI restriction fragments of a certain size (<1000 bases) to perform the assay. The benefit to using this approach is that each individual region would not have to be amplified separately. There would be the potential to screen thousands of SNPs from the single PCR reaction, i.e., multiplex potential.

Alternative methods for amplification of target nucleic acid sequences that may be used in the practice of the present invention are disclosed in U.S. Pat. Nos. 5,843,650, 5,846,709, 5,846,783, 5,849,546, 5,849,497, 5,849,547, 5,858,652, 5,866,366, 5,916,776, 5,922,574, 5,928,905, 5,928,906, 5,932,451, 5,935,825, 5,939,291 and 5,942,391, GB Application No. 2 202 328, and in PCT Application No. PCT/US89/01025, each of which is incorporated herein by reference in its entirety.

Qbeta Replicase, described in PCT Application No. PCT/US87/00880, may also be used as an amplification method in the present invention. In this method, a replicative sequence of RNA that has a region complementary to that of a target is added to a sample in the presence of an RNA polymerase. The polymerase will copy the replicative sequence, which may then be detected.

An isothermal amplification method, in which restriction endonucleases and ligases are used to achieve the amplification of target molecules that contain nucleotide 5'-[alpha-thio]-triphosphates in one strand of a restriction site may also be useful in the amplification of nucleic acids in the present invention (Walker et al., 1992). Strand Displacement Amplification (SDA), disclosed in U.S. Pat. No. 5,916,779, is another method of carrying out isothermal amplification of nucleic acids which involves multiple rounds of strand displacement and synthesis, i.e., nick translation.

Other nucleic acid amplification procedures include polymerization-based amplification systems (TAS), including nucleic acid sequence based amplification (NASBA) and 3SR (Kwoh et al., 1989; Gingeras et al., PCT Application WO 88/10315, incorporated herein by reference in their entirety). European Application No. 329 822 discloses a nucleic acid amplification process involving cyclically synthesizing single-stranded RNA (ssRNA), ssDNA, and double-stranded DNA (dsDNA), which may be used in accordance with the present invention.

PCT Application WO 89/06700 (incorporated herein by reference in its entirety) discloses a nucleic acid sequence amplification scheme based on the hybridization of a promoter region/primer sequence to a target single-stranded DNA (ssDNA) followed by polymerization of many RNA copies of the sequence. This scheme is not cyclic, i.e., new templates are not produced from the resultant RNA transcripts. Other amplification methods include "race" and "one-sided PCR" (Frohman, 1990; Ohara et al., 1989).

Another advantageous step is to prevent unincorporated NTPs from being incorporated in a subsequent primer extension reaction. Commercially available kits may be used to remove unincorporated NTPs from the amplification products. The use of shrimp alkaline phosphatase to destroy unincorporated NTPs is also a well-known strategy for this purpose.

5. Sequencing

DNA sequencing enables one to perform a thorough analysis of DNA because it provides the most basic information of all: the sequence of nucleotides. Maxam & Gilbert developed the first widely used sequencing methods—a "chemical cleavage protocol." Shortly thereafter, Sanger designed a procedure similar to the natural process of DNA replication. Even though both teams shared the 1980 Nobel Prize, Sanger's method became the standard because of its practicality.

Sanger's method, which is also referred to as dideoxy sequencing or chain termination, is based on the use of dideoxynucleotides (ddNTP's) in addition to the normal nucleotides (NTP's) found in DNA. Dideoxynucleotides are essentially the same as nucleotides except they contain a hydrogen group on the 3' carbon instead of a hydroxyl group (OH). These modified nucleotides, when integrated into a sequence, prevent the addition of further nucleotides. This occurs because a phosphodiester bond cannot form between the dideoxynucleotide and the next incoming nucleotide, and thus the DNA chain is terminated. Using this method, optionally coupled with amplification of the nucleic acid target, one can now rapidly sequence large numbers of target molecules, usually employing automated sequencing apparati. Such techniques are well known to those of skill in the art.

B. Detection Systems

1. Mass Spectrometry

By exploiting the intrinsic properties of mass and charge, mass spectrometry (MS) can resolved and confidently identified a wide variety of complex compounds. Traditional quantitative MS has used electrospray ionization (ESI) followed by tandem MS (MS/MS) (Chen et al., 2001; Zhong et al., 2001; Wu et al., 2000) while newer quantitative methods are being developed using matrix assisted laser desorption/ionization (MALDI) followed by time of flight (TOF) MS (Bucknall et al., 2002; Mirgorodskaya et al., 2000; Gobom et al., 2000).

i. ESI

ESI is a convenient ionization technique developed by Fenn and colleagues (Fenn et al., 1989) that is used to produce gaseous ions from highly polar, mostly nonvolatile biomolecules, including lipids. The sample is injected as a liquid at low flow rates (1-10 µL/min) through a capillary tube to which a strong electric field is applied. The field generates additional charges to the liquid at the end of the capillary and produces a fine spray of highly charged droplets that are electrostatically attracted to the mass spectrometer inlet. The evaporation of the solvent from the surface of a droplet as it travels through the desolvation chamber increases its charge density substantially. When this increase exceeds the Rayleigh stability limit, ions are ejected and ready for MS analysis.

A typical conventional ESI source consists of a metal capillary of typically 0.1-0.3 mm in diameter, with a tip held approximately 0.5 to 5 cm (but more usually 1 to 3 cm) away from an electrically grounded circular interface having at its center the sampling orifice, such as described by Kabarle et al. (1993). A potential difference of between 1 to 5 kV (but more typically 2 to 3 kV) is applied to the capillary by power supply to generate a high electrostatic field ($10^6$ to $10^7$ V/m) at the capillary tip. A sample liquid carrying the analyte to be analyzed by the mass spectrometer, is delivered to tip through an internal passage from a suitable source (such as from a chromatograph or directly from a sample solution via a liquid flow controller). By applying pressure to the sample in the capillary, the liquid leaves the capillary tip as a small highly electrically charged droplets and further undergoes desolvation and breakdown to form single or multi-charged gas phase ions in the form of an ion beam. The ions are then collected by the grounded (or negatively-charged) interface plate and led through an the orifice into an analyzer of the mass spectrometer. During this operation, the voltage applied to the capillary is held constant. Aspects of construction of ESI sources are described, for example, in U.S. Pat. Nos. 5,838,002; 5,788,166; 5,757,994; RE 35,413; and 5,986,258.

ii. ESI/MS/MS

In ESI tandem mass spectroscopy (ESI/MS/MS), one is able to simultaneously analyze both precursor ions and product ions, thereby monitoring a single precursor product reaction and producing (through selective reaction monitoring (SRM)) a signal only when the desired precursor ion is present. When the internal standard is a stable isotope-labeled version of the analyte, this is known as quantification by the stable isotope dilution method. This approach has been used to accurately measure pharmaceuticals (Zweigenbaum et al., 2000; Zweigenbaum et al., 1999) and bioactive peptides (Desiderio et al., 1996; Lovelace et al., 1991). Newer methods are performed on widely available MALDI-TOF instruments, which can resolve a wider mass range and have been used to quantify metabolites, peptides, and proteins. Larger molecules such as peptides can be quantified using unlabeled homologous peptides as long as their chemistry is similar to the analyte peptide (Duncan et al., 1993; Bucknall et al., 2002). Protein quantification has been achieved by quantifying tryptic peptides (Mirgorodskaya et al., 2000). Complex mixtures such as crude extracts can be analyzed, but in some instances sample clean up is required (Nelson et al., 1994; Gobom et al., 2000).

iii. SIMS

Secondary ion mass spectroscopy, or SIMS, is an analytical method that uses ionized particles emitted from a surface for mass spectroscopy at a sensitivity of detection of a few parts per billion. The sample surface is bombarded by primary energetic particles, such as electrons, ions (e.g., O, Cs), neutrals or even photons, forcing atomic and molecular particles to be ejected from the surface, a process called sputtering. Since some of these sputtered particles carry a charge, a mass spectrometer can be used to measure their mass and charge. Continued sputtering permits measuring of the exposed elements as material is removed. This in turn permits one to construct elemental depth profiles. Although the majority of secondary ionized particles are electrons, it is the secondary ions which are detected and analysis by the mass spectrometer in this method.

iv. LD-MS and LDLPMS

Laser desorption mass spectroscopy (LD-MS) involves the use of a pulsed laser, which induces desorption of sample material from a sample site—effectively, this means vaporization of sample off of the sample substrate. This method is usually only used in conjunction with a mass spectrometer, and can be performed simultaneously with ionization if one uses the right laser radiation wavelength.

When coupled with Time-of-Flight (TOF) measurement, LD-MS is referred to as LDLPMS (Laser Desorption Laser Photoionization Mass Spectroscopy). The LDLPMS method of analysis gives instantaneous volatilization of the sample, and this form of sample fragmentation permits rapid analysis without any wet extraction chemistry. The LDLPMS instrumentation provides a profile of the species present while the retention time is low and the sample size is small. In LDLPMS, an impactor strip is loaded into a vacuum chamber. The pulsed laser is fired upon a certain spot of the sample site, and species present are desorbed and ionized by the laser radiation. This ionization also causes the molecules to break up into smaller fragment-ions. The positive or negative ions made are then accelerated into the flight tube, being detected at the end by a microchannel plate detector. Signal intensity, or peak height, is measured as a function of travel time. The applied voltage and charge of the particular ion determines the kinetic energy, and separation of fragments are due to different size causing different velocity. Each ion mass will thus have a different flight-time to the detector.

One can either form positive ions or negative ions for analysis. Positive ions are made from regular direct photoionization, but negative ion formation require a higher powered laser and a secondary process to gain electrons. Most of the molecules that come off the sample site are neutrals, and thus can attract electrons based on their electron affinity. The negative ion formation process is less efficient than forming just positive ions. The sample constituents will also affect the outlook of a negative ion spectra.

Other advantages with the LDLPMS method include the possibility of constructing the system to give a quiet baseline of the spectra because one can prevent coevolved neutrals from entering the flight tube by operating the instrument in a linear mode. Also, in environmental analysis, the salts in the air and as deposits will not interfere with the laser desorption and ionization. This instrumentation also is very sensitive, known to detect trace levels in natural samples without any prior extraction preparations.

v. MALDI-TOF-MS

Since its inception and commercial availability, the versatility of MALDI-TOF-MS has been demonstrated convincingly by its extensive use for qualitative analysis. For example, MALDI-TOF-MS has been employed for the characterization of synthetic polymers (Marie et al., 2000; Wu et al., 1998). peptide and protein analysis (Roepstorff et al., 2000; Nguyen et al., 1995), DNA and oligonucleotide sequencing (Miketova et al., 1997; Faulstich et al., 1997; Bentzley et al., 1996), and the characterization of recombinant proteins (Kanazawa et al., 1999; Villanueva et al., 1999). Recently, applications of MALDI-TOF-MS have been extended to include the direct analysis of biological tissues and single cell organisms with the aim of characterizing endogenous peptide and protein constituents (Li et al., 2000; Lynn et al., 1999; Stoeckli et al., 2001; Caprioli et al., 1997; Chaurand et al., 1999; Jespersen et al., 1999).

The properties that make MALDI-TOF-MS a popular qualitative tool—its ability to analyze molecules across an extensive mass range, high sensitivity, minimal sample preparation and rapid analysis times—also make it a potentially useful quantitative tool. MALDI-TOF-MS also enables non-volatile and thermally labile molecules to be analyzed with relative ease. It is therefore prudent to explore the potential of MALDI-TOF-MS for quantitative analysis in clinical settings, for toxicological screenings, as well as for environmental analysis. In addition, the application of MALDI-TOF-MS to the quantification of peptides and proteins is particularly relevant. The ability to quantify intact proteins in biological tissue and fluids presents a particular challenge in the expanding area of proteomics and investigators urgently require methods to accurately measure the absolute quantity of proteins. While there have been reports of quantitative MALDI-TOF-MS applications, there are many problems inherent to the MALDI ionization process that have restricted its widespread use (Kazmaier et al., 1998; Horak et al., 2001; Gobom et al., 2000; Wang et al., 2000; Desiderio et al., 2000). These limitations primarily stem from factors such as the sample/matrix heterogeneity, which are believed to contribute to the large variability in observed signal intensities for analytes, the limited dynamic range due to detector saturation, and difficulties associated with coupling MALDI-TOF-MS to on-line separation techniques such as liquid chromatography. Combined, these factors are thought to compromise the accuracy, precision, and utility with which quantitative determinations can be made.

Because of these difficulties, practical examples of quantitative applications of MALDI-TOF-MS have been limited. Most of the studies to date have focused on the quantification of low mass analytes, in particular, alkaloids or active ingredients in agricultural or food products (Wang et al., 1999; Jiang et al., 2000; Wang et al., 2000; Yang et al., 2000; Wittmann et al., 2001), whereas other studies have demonstrated the potential of MALDI-TOF-MS for the quantification of biologically relevant analytes such as neuropeptides, proteins, antibiotics, or various metabolites in biological tissue or fluid (Muddiman et al., 1996; Nelson et al., 1994; Duncan et al., 1993; Gobom et al., 2000; Wu et al., 1997; Mirgorodskaya et al., 2000). In earlier work it was shown that linear calibration curves could be generated by MALDI-TOF-MS provided that an appropriate internal standard was employed (Duncan et al., 1993). This standard can "correct" for both sample-to-sample and shot-to-shot variability. Stable isotope labeled internal standards (isotopomers) give the best result.

With the marked improvement in resolution available on modern commercial instruments, primarily because of delayed extraction (Bahr et al., 1997; Takach et al., 1997), the opportunity to extend quantitative work to other examples is now possible; not only of low mass analytes, but also biopolymers. Of particular interest is the prospect of absolute multicomponent quantification in biological samples (e.g., proteomics applications).

The properties of the matrix material used in the MALDI method are critical. Only a select group of compounds is useful for the selective desorption of proteins and polypeptides. A review of all the matrix materials available for peptides and proteins shows that there are certain characteristics the compounds must share to be analytically useful. Despite its importance, very little is known about what makes a matrix material "successful" for MALDI. The few materials that do work well are used heavily by all MALDI practitioners and new molecules are constantly being evaluated as potential matrix candidates. With a few exceptions, most of the matrix materials used are solid organic acids. Liquid matrices have also been investigated, but are not used routinely.

2. Hybridization

There are a variety of ways by which one can assess genetic profiles, and may of these rely on nucleic acid hybridization. Hybridization is defined as the ability of a nucleic acid to selectively form duplex molecules with complementary stretches of DNAs and/or RNAs. Depending on the application envisioned, one would employ varying conditions of hybridization to achieve varying degrees of selectivity of the probe or primers for the target sequence.

Typically, a probe or primer of between 13 and 100 nucleotides, preferably between 17 and 100 nucleotides in length up to 1-2 kilobases or more in length will allow the formation of a duplex molecule that is both stable and selective. Molecules having complementary sequences over contiguous stretches greater than 20 bases in length are generally preferred, to increase stability and selectivity of the hybrid molecules obtained. One will generally prefer to design nucleic acid molecules for hybridization having one or more complementary sequences of 20 to 30 nucleotides, or even longer where desired. Such fragments may be readily prepared, for example, by directly synthesizing the fragment by chemical means or by introducing selected sequences into recombinant vectors for recombinant production.

For applications requiring high selectivity, one will typically desire to employ relatively high stringency conditions to form the hybrids. For example, relatively low salt and/or high temperature conditions, such as provided by about 0.02 M to about 0.10 M NaCl at temperatures of about 50° C. to about 70° C. Such high stringency conditions tolerate little, if any, mismatch between the probe or primers and the template or target strand and would be particularly suitable for isolating specific genes or for detecting specific mRNA transcripts. It is generally appreciated that conditions can be rendered more stringent by the addition of increasing amounts of formamide.

For certain applications, for example, lower stringency conditions may be used. Under these conditions, hybridization may occur even though the sequences of the hybridizing strands are not perfectly complementary, but are mismatched at one or more positions. Conditions may be rendered less stringent by increasing salt concentration and/or decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Hybridization conditions can be readily manipulated depending on the desired results.

In other embodiments, hybridization may be achieved under conditions of, for example, 50 mM Tris-HCl (pH 8.3), 75 mM KCl, 3 mM $MgCl_2$, 1.0 mM dithiothreitol, at temperatures between approximately 20° C. to about 37° C. Other hybridization conditions utilized could include approximately 10 mM Tris-HCl (pH 8.3), 50 mM KCl, 1.5 mM $MgCl_2$, at temperatures ranging from approximately 40° C. to about 72° C.

In certain embodiments, it will be advantageous to employ nucleic acids of defined sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of being detected. In preferred embodiments, one may desire to employ a fluorescent label or an enzyme tag such as urease, alkaline phosphatase or peroxidase, instead of radioactive or other environmentally undesirable reagents. In the case of enzyme tags, colorimetric indicator substrates are known that can be employed to provide a detection means that is visibly or spectrophotometrically detectable, to identify specific hybridization with complementary nucleic acid containing samples.

In general, it is envisioned that the probes or primers described herein will be useful as reagents in solution hybridization, as in PCR™, for detection of expression of corresponding genes, as well as in embodiments employing a solid phase. In embodiments involving a solid phase, the test DNA (or RNA) is adsorbed or otherwise affixed to a selected matrix or surface. This fixed, single-stranded nucleic acid is then subjected to hybridization with selected probes under desired conditions. The conditions selected will depend on the particular circumstances (depending, for example, on the G+C content, type of target nucleic acid, source of nucleic acid, size of hybridization probe, etc.). Optimization of hybridization conditions for the particular application of interest is well known to those of skill in the art. After washing of the hybridized molecules to remove non-specifically bound probe molecules, hybridization is detected, and/or quantified, by determining the amount of bound label. Representative solid phase hybridization methods are disclosed in U.S. Pat. Nos. 5,843, 663, 5,900,481 and 5,919,626. Other methods of hybridization that may be used in the practice of the present invention are disclosed in U.S. Pat. Nos. 5,849,481, 5,849,486 and 5,851,772. The relevant portions of these and other references identified in this section of the Specification are incorporated herein by reference.

3. Detectable Labels

Various nucleic acids may be visualized in order to confirm their presence, quantity or sequence. In one embodiment, the primer is conjugated to a chromophore but may instead be radiolabeled or fluorometrically labeled. In another embodiment, the primer is conjugated to a binding partner that carries a detectable moiety, such as an antibody or biotin. In other embodiments, the primer incorporates a fluorescent dye or label. In yet other embodiments, the primer has a mass label that can be used to detect the molecule amplified. Other embodiments also contemplate the use of Taqman™ and Molecular Beacon™ probes. Alternatively, one or more of the dNTPs may be labeled with a radioisotope, a fluorophore, a chromophore, a dye or an enzyme. Also, chemicals whose properties change in the presence of DNA can be used for detection purposes. For example, the methods may involve staining of a gel with, or incorporation into the separation media, a fluorescent dye, such as ethidium bromide or Vistra Green, and visualization under an appropriate light source.

The choice of label incorporated into the products is dictated by the method used for analysis. When using capillary electrophoresis, microfluidic electrophoresis, HPLC, or LC separations, either incorporated or intercalated fluorescent dyes are used to label and detect the amplification products. Samples are detected dynamically, in that fluorescence is quantitated as a labeled species moves past the detector. If any electrophoretic method, HPLC, or LC is used for separation, products can be detected by absorption of UV light, a property inherent to DNA and therefore not requiring addition of a label. If polyacrylamide gel or slab gel electrophoresis is used, the primer for the extension reaction can be labeled with a fluorophore, a chromophore or a radioisotope, or by associated enzymatic reaction. Alternatively, if polyacrylamide gel or slab gel electrophoresis is used, one or more of the NTPs in the extension reaction can be labeled with a fluorophore, a chromophore or a radioisotope, or by associated enzymatic reaction. Enzymatic detection involves binding an enzyme to a nucleic acid, e.g., via a biotin:avidin interaction, following separation of the amplification products on a gel, then detection by chemical reaction, such as chemiluminescence generated with luminol. A fluorescent signal can be monitored dynamically. Detection with a radioisotope or enzymatic reaction requires an initial separation by gel electrophoresis, followed by transfer of DNA molecules to a solid support (blot) prior to analysis. If blots are made, they can be analyzed more than once by probing, stripping the blot, and then reprobing. If the extension products are separated using a mass spectrometer no label is required because nucleic acids are detected directly.

In the case of radioactive isotopes, tritium, $^{14}$C and $^{32}$P are used predominantly. Among the fluorescent labels contemplated for use as conjugates include Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red.

4. Other Methods of Detecting Nucleic Acids

Other methods of nucleic acid detection that may be used in the practice of the instant invention are disclosed in U.S. Pat. Nos. 5,840,873, 5,843,640, 5,843,651, 5,846,708, 5,846,717, 5,846,726, 5,846,729, 5,849,487, 5,853,990, 5,853,992, 5,853,993, 5,856,092, 5,861,244, 5,863,732, 5,863,753, 5,866,331, 5,905,024, 5,910,407, 5,912,124, 5,912,145, 5,919,630, 5,925,517, 5,928,862, 5,928,869, 5,929,227, 5,932,413 and 5,935,791, each of which is incorporated herein by reference in its entirety.

5. Selection and of Primers/Probes/Enzymes

The present invention relies on the use of agents that are capable of detecting single nucleotide changes in DNA. These agents generally fall into two classes—agents that hybridize to target sequences that contain the change, and agents that hybridize to target sequences that are adjacent to (e.g., upstream or 5' to) the region of change. A third class of agents, restriction enzymes, do not hybridize, but instead cleave at a target site. A list of restriction enzymes can be found on the world-wide-web at fermentas.com/techinfo/re/prototypes.htm, hereby incorporated by reference.

6. Oligonucleotide Synthesis

Oligonucleotide synthesis is well known to those of skill in the art. Various mechanisms of oligonucleotide synthesis have been disclosed in for example, U.S. Pat. Nos. 4,659,774, 4,816,571, 5,141,813, 5,264,566, 4,959,463, 5,428,148, 5,554,744, 5,574,146, 5,602,244, each of which is incorporated herein by reference in its entirety. Basically, chemical synthesis can be achieved by the diester method, the triester method polynucleotides phosphorylase method and by solid-phase chemistry. These methods are discussed in further detail below.

Diester method. The diester method was the first to be developed to a usable state, primarily by Khorana and co-workers (Khorana, 1979). The basic step is the joining of two suitably protected deoxynucleotides to form a dideoxynucleotide containing a phosphodiester bond. The diester method is well established and has been used to synthesize DNA molecules (Khorana, 1979).

Triester method. The main difference between the diester and triester methods is the presence in the latter of an extra protecting group on the phosphate atoms of the reactants and products (Itakura et al., 1975). The phosphate protecting group is usually a chlorophenyl group, which renders the nucleotides and polynucleotide intermediates soluble in organic solvents. Therefore, purifications are done in chloroform solutions. Other improvements in the method include (i) the block coupling of trimers and larger oligomers, (ii) the extensive use of high-performance liquid chromatography for the purification of both intermediate and final products, and (iii) solid-phase synthesis.

Polynucleotide phosphorylase method. This is an enzymatic method of DNA synthesis that can be used to synthesize many useful oligodeoxynucleotides (Gillam et al., 1978). Under controlled conditions, polynucleotide phosphorylase adds predominantly a single nucleotide to a short oligodeoxynucleotide. Chromatographic purification allows the desired single adduct to be obtained. At least a trimer is required to initiate the method of adding one base at a time, a primer that must be obtained by some other method. The polynucleotide phosphorylase method works and has the advantage that the procedures involved are familiar to most biochemists.

Solid-phase methods. The technology developed for the solid-phase synthesis of polypeptides has been applied after an, it has been possible to attach the initial nucleotide to solid support material has been attached by proceeding with the stepwise addition of nucleotides. All mixing and washing steps are simplified, and the procedure becomes amenable to automation. These syntheses are now routinely carried out using automatic DNA synthesizers.

Phosphoramidite chemistry (Beaucage, 1993) has become by far the most widely used coupling chemistry for the synthesis of oligonucleotides. As is well known to those skilled in the art, phosphoramidite synthesis of oligonucleotides involves activation of nucleoside phosphoramidite monomer precursors by reaction with an activating agent to form activated intermediates, followed by sequential addition of the activated intermediates to the growing oligonucleotide chain (generally anchored at one end to a suitable solid support) to form the oligonucleotide product.

7. Separation of Nucleic Acids

In certain embodiments, nucleic acid products are separated by agarose, agarose-acrylamide or polyacrylamide gel electrophoresis using standard methods (Sambrook et al., 1989). Separated products may be cut out and eluted from the gel for further manipulation. Using low melting point agarose gels, the skilled artisan my remove the separated band by heating the gel, followed by extraction of the nucleic acid.

Separation of nucleic acids may also be effected by chromatographic techniques known in the art. There are many kinds of chromatography that may be used in the practice of the present invention, including capillary adsorption, partition, ion-exchange, hydroxylapatite, molecular sieve, reverse-phase, column, paper, thin-layer, and gas chromatography as well as HPLC.

A number of the above separation platforms can be coupled to achieve separations based on two different properties. For example, some of the primers can be coupled with a moiety that allows affinity capture, and some primers remain unmodified. Modifications can include a sugar (for binding to a lectin column), a hydrophobic group (for binding to a reverse-phase column), biotin (for binding to a streptavidin column), or an antigen (for binding to an antibody column). Samples are run through an affinity chromatography column. The flow-through fraction is collected, and the bound fraction eluted (by chemical cleavage, salt elution, etc.). Each sample is then further fractionated based on a property, such as mass, to identify individual components.

IV. Autoimmune Disease

A. Systemic Lupus Erythematosus

1. Definition and Symptoms

Systemic lupus erythematosus (SLE) is an autoimmune chronic inflammatory disease that most commonly affects the skin, joints, kidneys, heart, lungs, blood vessels, and brain. The most common symptoms include fatigue, muscle aches, low-grade fever, skin rashes, and kidney problems that are sometimes severe enough to require dialysis or transplant. Symptoms may also include a characteristic facial rash ("butterfly rash"), photosensitivity, and poor circulation to the extremities with cold exposure, known as Raynaud's phenomenon. Rheumatoid arthritis is another chronic autoimmune disease, and most people with SLE will develop arthritis during the course of their illness with similar symptoms to rheumatoid arthritis. Because SLE can affect the walls of the blood vessels, young women with SLE are at significantly higher risk for heart attacks from coronary artery disease. For many patients, alopecia occurs as SLE worsens.

Women who become pregnant with SLE are considered "high risk." These women have an increased risk of miscarriages, and the incidence of flares can increase with pregnancy. Antibodies from SLE can be transferred to the fetus, resulting in "neonatal lupus." Symptoms of neonatal lupus include anemia and skin rash, with congenital heart block being less common. Unlike SLE, neonatal lupus resolves after six months as the newborn metabolizes the mother's antibodies.

2. Diagnosis

Because the symptoms of SLE can vary widely, accurate diagnosis is difficult. A diagnosis of SLE is suggested for a patient who meets four or more of the eleven criteria established by the American Rheumatism Association, but there is currently no single test that establishes the diagnosis of SLE. However, these criteria are not definitive. The criteria are based on the symptoms of SLE, but also include the presence of anti-DNA, antinuclear (ANA), or anti-Sm antibodies, a false positive test for syphilis, anticardiolipin antibodies, lupus anticoagulant, or positive LE prep test. Some patients are diagnosed with SLE who manifest fewer than four criteria, while other such patients remain undiagnosed.

Most people with SLE test positive for ANA. Even so, the test is not definitive, as a number of conditions can cause a positive ANA test. Other antibody tests that can aid in a diagnosis of SLE or other autoimmune conditions include anti-RNP, anti-Ro (SSA), and anti-La (SSB).

3. Treatment

There is currently no cure for SLE, and the illness remains characterized by alternating periods of illness, or flares, and periods of wellness, or remission. The current goal of treatment is to relieve the symptoms of SLE, and to protect the organ systems affected by decreasing the level of autoimmune activity. More and better quality rest is prescribed for fatigue, along with exercise to maintain joint strength and range of motion. DHEA (dehydroepiandrosterone) can reduce fatigue and thinking problems associated with SLE. Physicians also commonly prescribe Nonsteroidal antiinflammatory drugs (NSAIDs) for pain and inflammation, although this can cause stomach pain and even ulcers in some patients.

Hydroxychloroquine, an anti-malarial medication, can be effective in treating fatigue related to SLE as well as skin and joint problems. Hydroxychloroquine also decreases the frequency of excessive blood clotting in some SLE patients. Corticosteroids are needed for more serious cases, although the serious side effects, such as weight gain, loss of bone mass, infection, and diabetes limits the length of time and dosages at which they can be prescribed. Immunosuppressants, or cytotoxic drugs, are used to treat severe cases of SLE, but again serious side effects such as increased risk of infection from decreased blood cell counts are common.

Possible future therapies include stem cell transplants to replace damaged immune cells and radical treatments that would temporarily kill all immune system cells. Other future treatments may include "biologic agents" such as the genetically engineered antibody rituximab (anti-CD20) that block parts of the immune system, such as B cells. Recently, two groups of researchers found that even partial restoration of function of an inhibitory Fc receptor prevented the development of SLE in several strains of mice that were genetically prone to the disease. Reviewed in Kuehn, Lupus (2005).

4. Who SLE Affects

SLE is much more common among women than men, with women comprising approximately 90% of all SLE patients. It is also three times more common in African American women than in women of European descent, although the incidence is also higher among women of Japanese and Chinese ancestry.

Because widely varying symptoms of SLE make accurate diagnosis difficult, the exact number of people who suffer from SLE is unknown. The Lupus Foundation of America, however, estimates that approximately 1,500,000 Americans have some form of lupus. The prevalence of SLE is estimated to be about 40 per 100,000.

B. Other Autoimmune Diseases

1. Rheumatoid Arthritis

The exact etiology of RA remains unknown, but the first signs of joint disease appear in the synovial lining layer, with proliferation of synovial fibroblasts and their attachment to the articular surface at the joint margin (Lipsky, 1998). Subsequently, macrophages, T cells and other inflammatory cells are recruited into the joint, where they produce a number of mediators, including the cytokines interleukin-1 (IL-1), which contributes to the chronic sequalae leading to bone and cartilage destruction, and tumour necrosis factor (TNF-$\alpha$), which plays a role in inflammation (Dinarello, 1998; Arend & Dayer, 1995; van den Berg, 2001). The concentration of IL-1 in plasma is significantly higher in patients with RA than in healthy individuals and, notably, plasma IL-1 levels correlate with RA disease activity (Eastgate et al., 1988). Moreover, synovial fluid levels of IL-1 are correlated with various radiographic and histologic features of RA (Kahle et al., 1992; Rooney et al., 1990).

In normal joints, the effects of these and other proinflammatory cytokines are balanced by a variety of anti-inflammatory cytokines and regulatory factors (Burger & Dayer, 1995). The significance of this cytokine balance is illustrated in juvenile RA patients, who have cyclical increases in fever throughout the day (Prieur et al., 1987). After each peak in fever, a factor that blocks the effects of IL-1 is found in serum and urine. This factor has been isolated, cloned and identified as IL-1 receptor antagonist (IL-1ra), a member of the IL-1 gene family (Hannum et al., 1990). IL-1ra, as its name indicates, is a natural receptor antagonist that competes with IL-1 for binding to type I IL-1 receptors and, as a result, blocks the effects of IL-1 (Arend et al., 1998). A 10- to 100-fold excess of IL-1ra may be needed to block IL-1 effectively; however, synovial cells isolated from patients with RA do not appear to produce enough IL-1ra to counteract the effects of IL-1 (Firestein et al., 1994; Fujikawa et al., 1995).

2. Sjögren's Syndrome

Primary Sjögren's syndrome (SS) is a chronic, slowly progressive, systemic autoimmune disease, which affects predominantly middle-aged women (female-to-male ratio 9:1), although it can be seen in all ages including childhood (Jonsson et al., 2002). It is characterized by lymphocytic infiltration and destruction of the exocrine glands, which are infiltrated by mononuclear cells including CD4+, CD8+ lymphocytes and B-cells (Jonsson et al., 2002). In addition, extraglandular (systemic) manifestations are seen in one-third of patients (Jonsson et al., 2001).

The glandular lymphocytic infiltration is a progressive feature (Jonsson et al., 1993), which, when extensive, may replace large portions of the organs. Interestingly, the glandular infiltrates in some patients closely resemble ectopic lymphoid microstructures in the salivary glands (denoted as ectopic germinal centers) (Salomonsson et al., 2002; Xanthou & Polihronis, 2001). In SS, ectopic GCs are defined as T and B cell aggregates of proliferating cells with a network of follicular dendritic cells and activated endothelial cells. These GC-like structures formed within the target tissue also portray functional properties with production of autoantibodies (anti-Ro/SSA and anti-La/SSB) (Salomonsson et al., 2003).

In other systemic autoimmune diseases, such as RA, factors critical for ectopic GCs have been identified. Rheumatoid synovial tissues with GCs were shown to produce chemokines CXCL13, CCL21 and lymphotoxin (LT)-$\beta$ (detected on follicular center and mantle zone B cells). Multivariate regression analysis of these analytes identified CXCL13 and LT-$\beta$ as the solitary cytokines predicting GCs in rheumatoid synovitis (Weyand & Goronzy, 2003). Recently CXCL13 and CXCR5 in salivary glands has been shown to play an essential role in the inflammatory process by recruiting B and T cells, therefore contributing to lymphoid neogenesis and ectopic GC formation in SS (Salomonsson et al., 2002.)

3. Autoimmune Diseases

The following is a list of autoimmune diseases may be subject to analysis using the target SNPs discussed herein: juvenile onset diabetes mellitus, Wegener's granulomatosis, inflammatory bowel disease, polymyositis, dermatomyositis, multiple endocrine failure, Schmidt's syndrome, autoimmune uveitis, Addison's disease, adrenalitis, Graves' disease, thyroiditis, Hashimoto's thyroiditis, autoimmune thyroid disease, pernicious anemia, gastric atrophy, chronic hepatitis, lupoid hepatitis, atherosclerosis, presenile dementia, demyelinating diseases, multiple sclerosis, subacute cutaneous lupus erythematosus, hypoparathyroidism, Dressler's syndrome, myasthenia gravis, autoimmune thrombocytopenia, idiopathic thrombocytopenic purpura, hemolytic anemia, pemphigus vulgaris, pemphigus, dermatitis herpetiformis, alopecia arcata, pemphigoid, scleroderma, progressive systemic sclerosis, CREST syndrome (calcinosis, Raynaud's phenomenon, esophageal dysmotility, sclerodactyly, and telangiectasia), adult onset diabetes mellitus (Type II diabetes), male and female autoimmune infertility, ankylosing spondolytis, ulcerative colitis, Crohn's disease, mixed connective tissue disease, polyarteritis nedosa, systemic necrotizing vasculitis, juvenile onset rheumatoid arthritis, glomerulonephritis, atopic dermatitis, atopic rhinitis, Goodpasture's syndrome, Chagas' disease, sarcoidosis, rheumatic fever, asthma, recurrent abortion, anti-phospholipid syndrome, farmer's lung, erythema multiforme, post cardiotomy syndrome, Cushing's syndrome, autoimmune chronic active hepatitis, bird-fancier's lung, allergic disease, allergic encephalomyelitis, toxic epidermal necrolysis, alopecia, Alport's syndrome, alveolitis, allergic alveolitis, fibrosing alveolitis, interstitial lung disease, erythema nodosum, pyoderma gangrenosum, transfusion reaction, leprosy, malaria, leishmaniasis, trypanosomiasis, Takayasu's arteritis, polymyalgia rheumatica, temporal arteritis, schistosomiasis, giant cell arteritis, ascariasis, aspergillosis, Sampter's syndrome, eczema, lymphomatoid granulomatosis, Behcet's disease, Caplan's syndrome, Kawasaki's disease, dengue, encephalomyelitis, endocarditis, endomyocardial fibrosis, endophthalmitis, erythema elevatum et diutinum, psoriasis, erythroblastosis fetalis, eosinophilic faciitis, Shulman's syndrome, Felty's syndrome, filariasis, cyclitis, chronic cyclitis, heterochronic cyclitis, Fuch's cyclitis, IgA nephropathy, Henoch-Schonlein purpura, glomerulonephritis, graft versus host disease, transplantation rejection, human immunodeficiency virus infection, echovirus infection, cardiomyopathy, Alzheimer's disease, parvovirus infection, rubella virus infection, post vaccination syndromes, congenital rubella infection, Hodgkin's and Non-Hodgkin's lymphoma, renal cell carcinoma, multiple myeloma, Eaton-Lambert syndrome, relapsing polychondritis, malignant melanoma, cryoglobulinemia, Waldenstrom's macroglobulemia, Epstein-Barr virus infection, mumps, Evan's syndrome, and autoimmune gonadal failure.

V. Kits

All the essential materials and reagents required for detecting SNPs in a sample may be assembled together in a kit. This generally will comprise a primer or probe designed to hybridize specifically to or upstream of target nucleotides of the polymorphism of interest. The primer or probe may be labeled with a radioisotope, a fluorophore, a chromophore, a dye, an enzyme, or TOF carrier. Also included may be enzymes suitable for amplifying nucleic acids, including various polymerases (reverse transcriptase, Taq, etc.), dNTPs/rNTPs and buffers (e.g., 10× buffer=100 mM Tris-HCl (pH 8.3), and 500 mM KCl) to provide the necessary reaction mixture for amplification. One or more of the deoxynucleotides may be labeled with a radioisotope, a fluorophore, a chromophore, a dye, or an enzyme. Such kits may also include enzymes and other reagents suitable for detection of specific nucleic acids or amplification products.

The container means of the kits will generally include at least one vial, test tube, flask, bottle, or other container means, into which a component may be placed, and preferably, suitably aliquoted. Where there is more than one component in the kit, the kit also will generally contain additional containers into which the additional components may be separately placed. However, various combinations of components may be comprised in a container. The kits of the present invention also will typically include a means for packaging the component containers in close confinement for commercial sale. Such packaging may include injection or blow-molded plastic containers into which the desired component containers are retained.

VI. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Methods

With their collaborators, Dr. David Altshuler and Dr. Robert Graham at the Broad Institute at MIT, the inventors designed and performed a GWAS using the MN SLE family collection. The clinical and demographic features of this cohort have been well described (Gaffney 1998; Gaffney 2000; Gaffney 2006) and all cases meet 1982 revised ACR criteria for SLE. The basic design of the study was a case/control format using 478 unrelated Caucasian female SLE subjects. An Affymetrix 500K 5.0 SNP array was used as the genotyping platform. Each case was matched in a ratio of 1:5 with Caucasian controls from either the Welcome Trust Case Control consortium or the National Institute of Mental Health (world-wide-web at nimhgenetics.org) genotyped on the same Affymetrix platform as the study saving us tremendous expense in control genotyping. Furthermore, the ability to do 1:5 case/control matching substantially increases genetic power since the large number of controls results in more accurate estimates of control allele frequencies. To address population stratification, cases and controls were genetically matched using the identity by state (IBS) clustering method implemented in the PLINK software package developed by Shaun Purcell at Broad (pngu.mgh.harvard.edu/~purcell/plink/). As a further safeguard against population stratification, the inventors genotyped unaffected parents from 231 (231 complete trios) of the 478 SLE subjects thus allowing data analysis using family-based association methods. The inventors believe the case/control design with embedded family-based pedigrees is a particularly unique feature of this study.

The effectiveness of IBS matching was measured using Eigenstrat, which revealed problems matching 45 cases/235 controls. These samples were removed from the final analysis. Following application of all QC parameters (individuals with >10% missing genotypes, SNPs with >10% missing data or HWE p-values <0.0001 were excluded) the inventors' final data set contained 433 SLE cases, 2165 controls and 314,000 SNPs. The final chi-square inflation factor ($\lambda$) was 1.06 and all test statistics were corrected accordingly.

Example 2

Results

Figure 2:
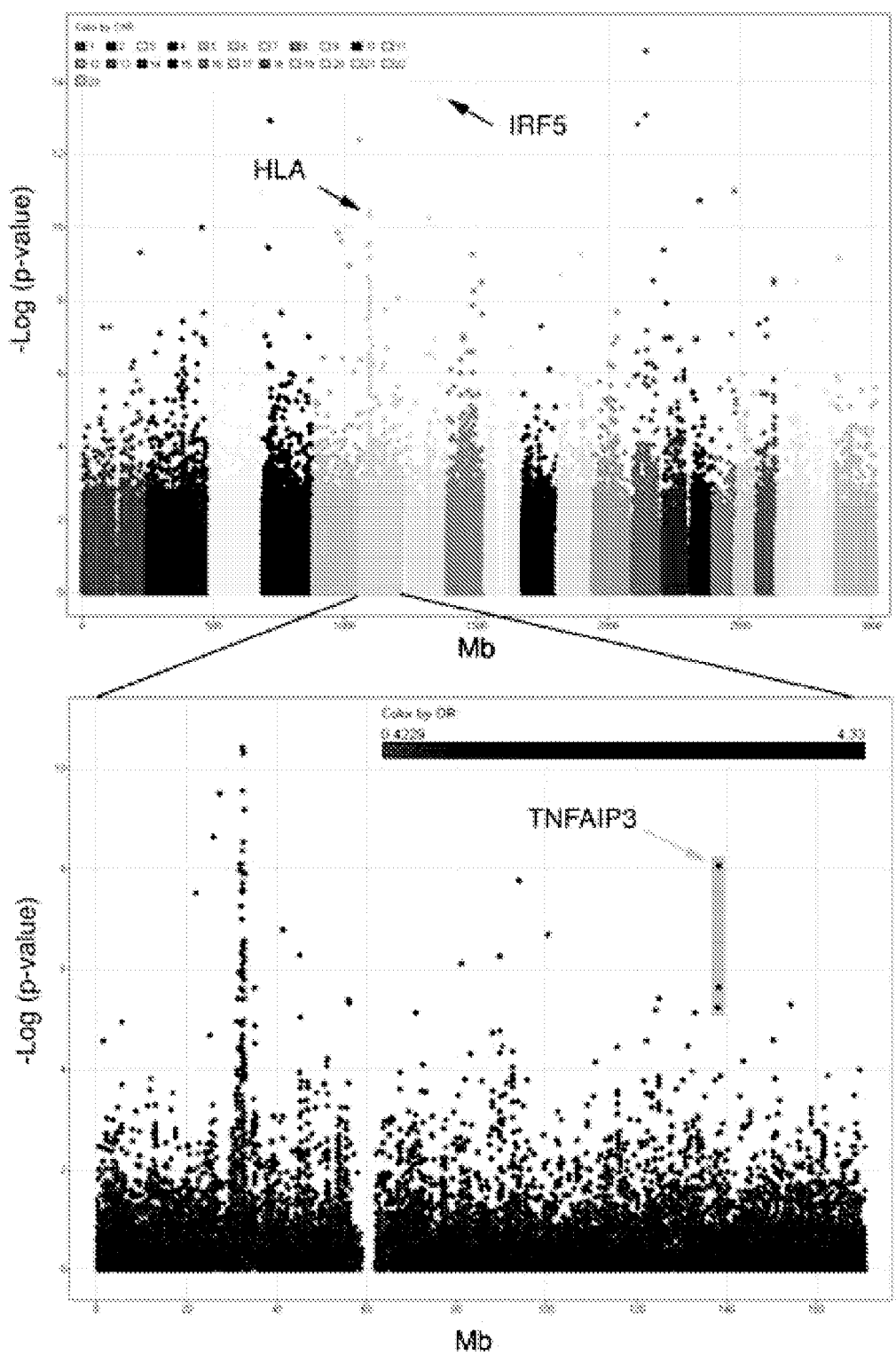
FIG. 2. Results from GWAS of 433 SLE cases and 2165 controls genotyped on the Affymetrix 500K 5.0 array. Data points are shaded according to chromosome. Expected association in the HLA and IRF5 regions are indicated. The lower panel shows an expanded view of chromosome 6. The HLA region can be seen at 32 Mb. TNFAIP3 is highlighted in the gray rectangle.

The results of the analysis for all 314,000 SNPs is shown in FIG. 2, top panel. Reassuringly, the inventors readily identified the expected strong association in the HLA region and IRF5 locus (Graham 2006) (marked by arrows on the figure). To further investigate the strongest effects the inventors filtered the results based on p-values for the case/control analysis setting a strict genome-wide cutoff ($p<10^{-6}$) followed by a TDT p-value filter ($p<0.01$). Nineteen SNPs met these conservative criteria. They then manually evaluated the cluster plots and determined that 2 SNPs clustered poorly which likely accounted for their very small p-values. The remaining 17 SNPs displayed tight, cleanly defined clusters consistent with a robust assay. Fourteen of these SNPs mapped to the HLA region and one mapped to IRF5.

Two novel associations were observed: RAD54B (rs6997115, OR=1.43, $p=8.99\times10^{-7}$) and TNFAIP3 (rs5029939, OR=2.29, $p=8.49\times10^{-9}$). RAD54B is a member of the SNF2/SWI2 superfamily and is part of a complex involved in the recombinational repair of DNA damage (Hiramoto et al., 1999). Mutations of RAD54B have been shown to be associated with lymphoma and various carcinomas (Hiramoto 1999), however no defined role for RAD54B in the immune system has been identified. On the other hand, TNFAIP3 represented a spectacular SLE candidate gene given its central role in attenuating NF-κB signaling and controlling inflammation (FIG. 2, bottom panel, gray box).

Figure 3:
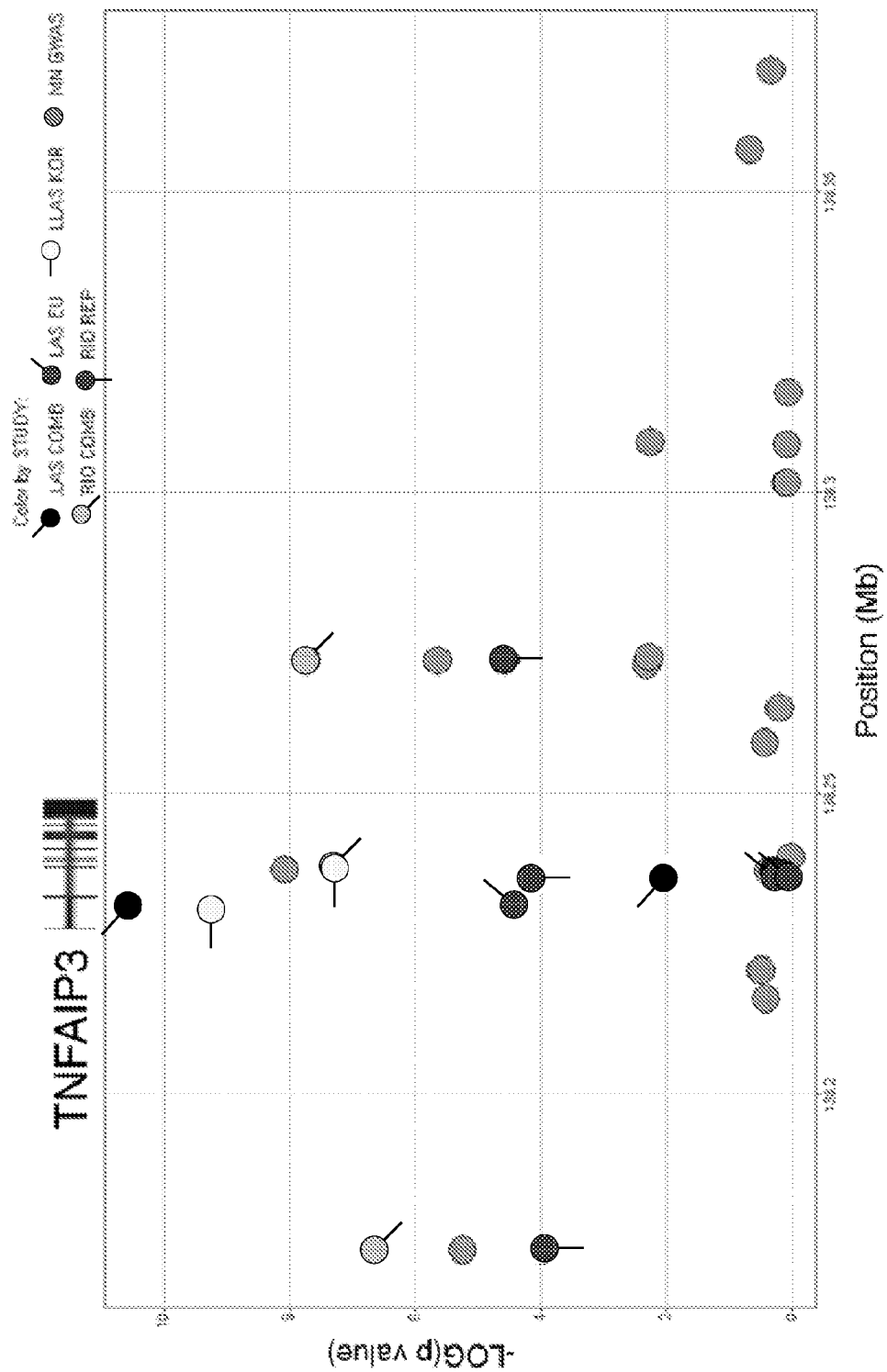
FIG. 3. Association of TNFAIP3 with SLE. Data from four sources are presented as discussed in the text: European Americans (EU) LLAS (◆) and Korean LLAS (-●) are, respectively, European-derived and Korean results from the Oklahoma large lupus association study (LLAS); LLAS Comb (●) is the combined results for the LLAS data. MN GWAS (●) are the data from samples collected at the University of Minnesota that are now at OMRF, Trio Rep (●) are the data from 265 and 455 complete trios from the GenES study and UK, respectively; Trio Comb (●) is the entire set of available trios including 231 from the UMN collection typed in the GWAS.

The inventors next looked more closely at the association evidence for the 19 SNPs in the TNFAIP3 region available on the Affymetrix SNP array. These data are summarized in FIG. 3 and Table 1. In the GWAS dataset (FIG. 3, gray circles) three SNPs were associated with $p<10^{-5}$. The peak association was at rs5029939, which produced a $\chi^2=33.16$ and $p=8.47\times10^{-9}$ (Table 1). This SNP is located in the second intron of TNFAIP3 and didn't appear to disrupt any known regulatory motif. Two other SNPs, rs10499197 located 63.2 kb upstream and rs7749323 located 34.7 kb downstream (outside of the gene) also demonstrated association $p=5.63\times10^{-6}$ and $p=2.26\times10^{-6}$, respectively (FIG. 3, gray circles, Table 1).

5,459 controls from five different ethnic groups. Genotyping data from 670 Korean SLE cases and 785 controls and 1,071 European American cases and 2,015 controls are now available and summarized in FIG. 3 and Table 1. The TNFAIP3 SNPs genotyped in LLAS (rs3757173, rs629953, rs5029938) were selected before the results of the MN GWAS study were available but are in close proximity to the rs5029939 SNP and lie within the gene.

TABLE 1

Summary of Top Scoring SNPs in TNFAIP3

| SNP | rs10499197 | rs3757173 | rs629953 | rs5029939 | rs7749323 |
|---|---|---|---|---|---|
| Position | 138.174209 | 138.231847 | 138.236734 | 138.237416 | 138.272082 |
| Minor Allele | G | C | T | G | A |
| MAF (Caucasians) | 3.2 | 8.3 | 35.9 | 3.4 | 3.2 |
| GWAS (433 cases/2165 controls) | | | | | |
| Chi-Square | 20.61 | | | 33.16 | 22.36 |
| P Value | 5.63E−06 | | | 8.47E−09 | 2.26E−06 |
| Odds Ratio | 2.00 | | | 2.29 | 2.06 |
| 95% CI | 1.47-2.73 | | | 1.71-3.06 | 1.52-2.81 |
| Trio Replication (720 trios) | | | | | |
| Chi-Square | 15.06 | | | 15.37 | 17.61 |
| P Value | 1.04E−04 | | | 8.86E−05 | 2.71E−05 |
| Trio Combined* (951 trios) | | | | | |
| Chi-Square | 26.26 | | | 29.13 | 31.61 |
| P Value | 2.99E−07 | | | 6.78E−08 | 1.88E−08 |
| LLAS EU (1071 cases/2015 controls) | | | | | |
| Chi-Square | | 16.52 | 0.1015 | | |
| P Value | | 4.81E−05 | 0.75 | | |
| Odd Ratio | | 1.37 | 1.02 | | |
| 95% CI | | 1.18-1.61 | 0.92-1.12 | | |
| LLAS Korean (670 cases/785 controls) | | | | | |
| Chi-Square | | 36.75 | 28.99 | | |
| P Value | | 1.35E−09 | 7.28E−08 | | |
| Odd Ratio | | 2.21 | 1.75 | | |
| 95% CI | | 1.70-2.86 | 1.42-2.14 | | |
| LLAS Combined (1741 cases/2800 controls) | | | | | |
| Chi-Square | | 43.88 | 7.06 | | |
| P Value | | 3.50E−11 | 0.00788 | | |
| Odd Ratio | | 1.56 | 1.12 | | |
| 95% CI | | 1.37-1.78 | 1.03-1.34 | | |

*Includes 231 UMN trios used in the GWAS

The next step was to determine if the association with TNFAIP3 could be replicated in independent SLE subjects. The first replication set consisted of 720 complete Caucasian trios (265 from the Canadian Genetic and Environment in SLE (GenES) study (P. I. John Rioux) and 455 from the United Kingdom (P. I. Tim Vyse)). In this replication experiment, the inventors genotyped the same three SNPs (rs10499197, rs5029939, rs7749323) that demonstrated strong association in the GWAS. The results of this experiment are shown in FIG. 3 (red circles) and Table 1. Again, the inventors noted evidence for association with all three SNPs. In this dataset, SNP rs7749323 was most associated producing a $\chi^2=17.6$, $p=2.71\times10^{-5}$. When these results were combined with the 231 trios from the GWAS study, all three SNPs achieved genome-wide significant p values $<10^{-6}$ (FIG. 3, green circles, Table 1).

The second replication dataset comes from a case-control study is referred as the Large Lupus Association Study (LLAS) currently underway at the Oklahoma Medical Research Foundation (OMRF). The inventors are evaluating over 19,000 SNPs in ~10,000 subjects. When complete, they will have genotype data in TNFAIP3 from in 5,849 cases and In the Korean samples (FIG. 3, yellow circles, Table 1), two of three SNPs were associated while the third SNP (rs5029938) was monomorphic in this population (data not shown). The peak association was at rs3757173, which produced a $\chi^2=36.8$ and $p=1.35\times10^{-9}$. This SNP is located in the first intron of TNFAIP3 approximately 5.5 kb upstream of rs5029929, the top scoring SNP in the GWAS. The next SNP, rs629953 was also associated with a $p=7.28\times10^{-8}$. Although only 37% of the European-American samples have been genotyped to date, preliminary analysis indicates that at least 1 of the 3 TNFAIP3 SNPs (rs3757173, $\chi^2=16.5$, $p=4.81\times10^{-5}$) is associated in European-Americans (FIG. 3, blue circles, Table 1). For marker rs3757173 the two LLAS populations produce a combined p value=$3.5\times10^{-11}$ (FIG. 3, black circle, Table 1). Importantly, in each of these datasets the inventors observe the minor allele to be enriched in SLE subjects (case/control) or overtransmitted to affected offspring (TDT).

The inventors then evaluated the haplotypic relationship between the top five scoring SNPs in the TNFAIP3 locus using HapMap data from the CEU population (FIG. 4). All five markers demonstrate strong LD as measured by D'. However, only the three markers originally typed in the GWAS study (rs10499197, rs5029939, rs7749323) demonstrated reasonably high correlation ($r^2$.79-1). The associated alleles for these three markers are carried on a rare haplotype present in about 3.3% of CEU HapMap chromosomes (FIG. 4, arrow). The MAF for these SNPs in HapMap closely resemble the MAF seen in the control samples (Table 2).

In summary, the inventors have identified five SNPs in TNFAIP3, a critical regulator of NF-κB signaling, that associate SLE. First, the genetic effects are strong and meet genome-wide criteria for association. Second, these results replicate in at least two independent SLE cohorts using both case/control and family-based methods. Third, genetic association with TNFAIP3 is a highly novel observation and no papers currently exist in the literature directly linking TNFAIP3 with human autoimmunity. And fourth, the central role that TNFAIP3 has in controlling NF-κB signaling and modulating inflammatory responses make TNFAIP3 a compelling candidate for autoimmunity.

Example 4

Results

Five SNPs met the criteria described above (Table 2). The results of the meta-analysis clearly demonstrate the strength of the association within the TNFAIP3 locus with all SNPs but one (rs375173) exceeding strict genome-wide criteria ($P<1\times10^{-8}$) for association (Table 2). SNP rs5029939, the SNP demonstrating the strongest association evidence in the inventors' LuMNAS GWAS study was genotyped in 3 out of the 4 samples sets and produced convincing a meta-analysis p-value of $1.51\times10^{-15}$ clearly validating this association as an SLE risk effect. Of particular interest are the odds ratios which are ~2.0 for four of the five variants shown. To the inventors' knowledge, the HLA locus is the only other validated SLE locus that presents with OR higher than 2; thus, they interpret this to mean that the TNFAIP3 risk effect carries significant genetic potency.

TABLE 2

Meta-analysis of association data in the region of TNFAIP3

| SNP | Assoc Allele | LuMNAS GWAS Case (N = 431) | LuMNAS GWAS Control (N = 2155) | LuMNAS TRIO Families (N = 740) Trans:Untrans | BE2 Case (N = 1022) | BE2 Control (N = 1226) | LLAS Case (N = 1278) | LLAS Control (N = 1774) | Meta P | OR |
|---|---|---|---|---|---|---|---|---|---|---|
| rs10499197 | G | 0.0603 | 0.0302 | 109:46 | | | | | $2.52 \times 10-11$ | 2.06 |
| rs3757173 | C | | | | 0.1080 | 0.0737 | 0.1017 | 0.0781 | $5.79 \times 10-07$ | 1.41 |
| rs5029939 | G | 0.0696 | 0.0314 | 131:57 | 0.0580 | 0.0307 | | | $1.51 \times 10-15$ | 2.09 |
| rs2230926 | G | | | 124:59 | 0.0575 | 0.0307 | | | $1.64 \times 10-09$ | 2.02 |
| rs7749323 | A | 0.0615 | 0.0300 | 117:46 | | | | | $8.33 \times 10-13$ | 2.12 |

Example 3

Methods

The BE2 dataset is a case/control dataset comprised of 1313 SLE cases and 1226 controls selected from among those available through the Lupus Family Registry and Repository (LFRR) and University of Minnesota collections. There were 291 SLE cases in common between the LuMNAS GWAS and BE2 resulting in 1022 independent SLE cases available for the meta-analysis. The LLAS (Large Lupus Association Study) study is a multi-ethnic case/control association study performed at the OMRF in late 2007. In the LLAS study, 11,695 subjects (cases and controls) were genotyped using 20,506 SNPs producing over 239 million genotypes. A subset of samples and SNPs from the LLAS served as the primary replication dataset for the recently published SLEGEN consortium GWAS (Harley et al., 2008). From among the 3072 European American (EA) SLE cases and 3102 EA controls genotyped in LLAS, 1278 cases and 1774 controls were independent of LuMNAS and BE2 and thus available for inclusion in the meta-analysis. In total, there was 2371 independent SLE cases and 5155 independent controls available for the meta-analysis. SNPs were chosen for inclusion in the meta-analysis if they were genotyped in a minimum of two datasets and demonstrated evidence of association (P<0.01) in at least one dataset. The meta-analysis was performed by combining the odds ratios between the studies using the Cochran Mantel-Haenzel method in SAS v. 9.1. SNPs genotyped in the LuMNAS Trio replication study (N=4) were combined with the meta-analysis case/control p-values using Fisher's method (Fisher, 1925).

This meta-analysis represents the largest dataset yet assembled characterizing the genetic effect of variants in the region of TNFAIP3 and emphasizes the strength and persistence of the genetic association across multiple independent SLE sample sets. Based on these results, the inventors confidently conclude that the genetic association between variants in TNFAIP3 and SLE is secure and the experiments proposed in this proposal are warranted and highly relevant.

Figure 5:
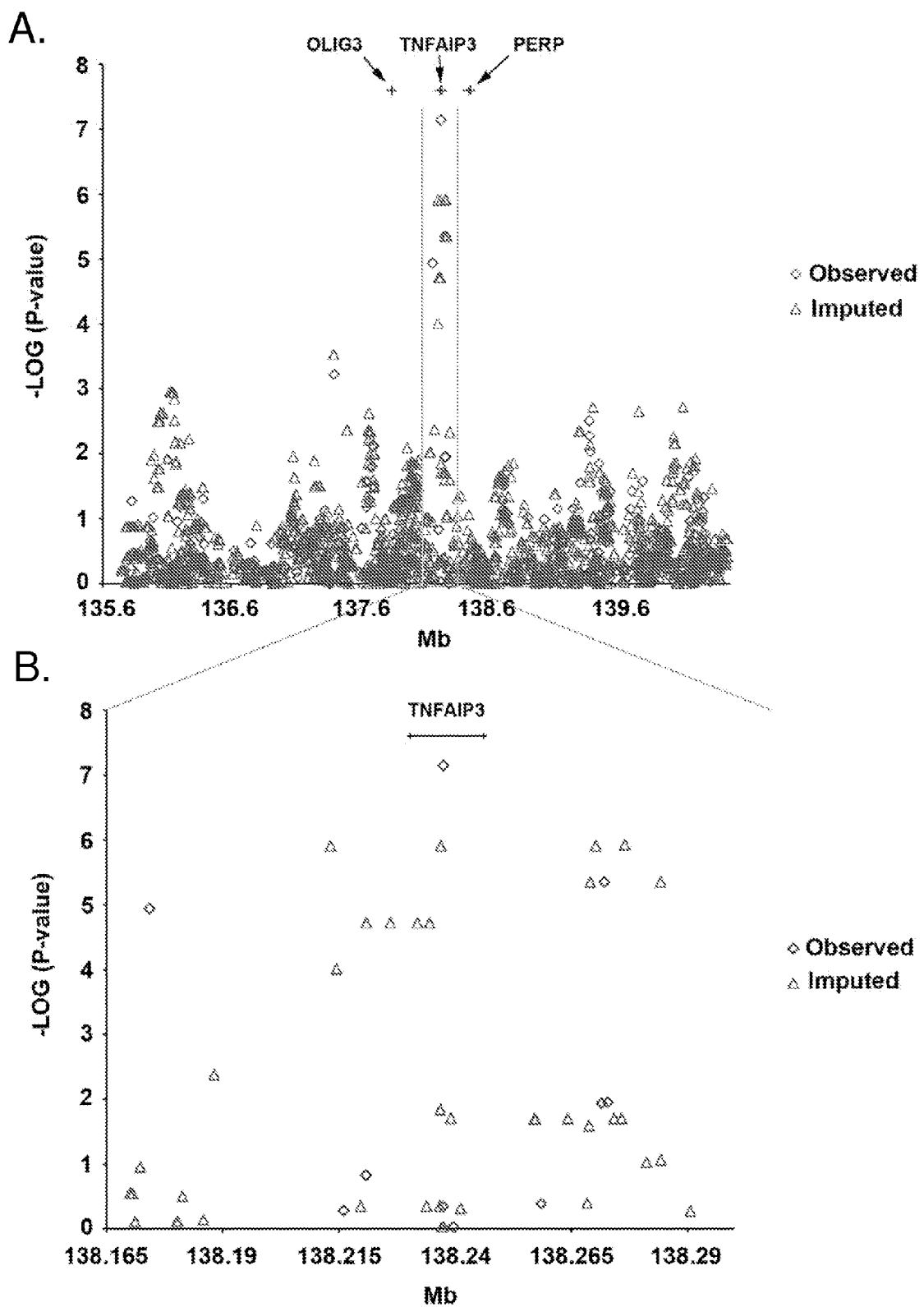
FIGS. 5A-B. Results of Imputation Across a 5 MB Region Centered on TNFAIP3.

Next, the inventors imputed genotypes from the Phase II HapMap to determine if untyped variants contributed to the genetic association in the region of TNFAIP3 and to better define the boundaries of the TNFAIP3 SLE risk haplotype. They chose to impute over a 5 MB interval centered on TNFAIP3 from marker rs4896151 (135,871,489) to marker rs1977772 (140,734,001) on chromosome 6q. This interval includes 20 genes in addition to TNFAIP3, some with a possible role in immune system function including interleukin 20 receptor α (IL20Rα), interleukin 22 receptor α (IL22Rα), interferon γ receptor 1 (INFγR1) and mitogen-activated protein kinase kinase kinase 5 (MAP3K5). Imputation was performed by merging the LuMNAS GWAS genotype data from the 5 MB interval flanking TNFAIP3 and with HapMap Phase II data from the same region using PLINK (FIGS. 5A-B). Imputation was also performed using the IMPUTE package with nearly identical results (Marchini et al., 2007). This process generated a list of SNPs for which differences in strand orientation prohibited further merging of the data. The strand orientation of these SNPs was "flipped" in the HapMap genotype file to match the strand orientation for the LuMNAS data file. SNPs with A/T or G/C alleles cannot be detected by PLINK and were corrected manually. Once the merged dataset was assembled, the inventors imputed the genotype data using the "proxy_impute" PLINK command.

The original LuMNAS dataset included 390 SNPs in the 5 MB interval. Following imputation, data were available for 3670 SNPs, a nearly 10-fold increase in the number of SNPs. As a quality control measure, they filtered the imputed dataset for SNPs that demonstrated information scores<0.7 and/or NPRX (number of proxy SNPs used to impute the SNP) scores≦2 (N=1173). This resulted in a final imputed dataset of 2497 SNPs (FIGS. 5A-B).

The results of the imputation clearly demonstrate the association peak centered under TNFAIP3 comprised of both observed SNPs (blue diamonds) and imputed SNPs (red triangles). No other region in the 5 MB interval reached significance at $P<10^{-4}$. In contrast, eleven imputed SNPs near TNFAIP3 demonstrated association with SLE at $P<10^{-4}$ (Table 3). Imputation accuracy for all eleven SNPs was >99% and for the three observed SNPs (rs10499197, rs5029939, rs7749323) the concordance rates between observed genotypes and imputed genotypes exceeded 99% indicating robust imputation over this region. No imputed SNP exceeded the best observed SNP (rs5029939) in terms of p-value (Table 3). The exon 3 missense SNP rs2230926 is not included in these results as it did not perform well in the imputation. The imputation also defined the extent of the risk haplotype in the region of TNFAIP3. Before imputation, association with SNPs on the 3' end extended as far as rs7749323. Following imputation, additional SNPs extend the risk haplotype ~12 kb downstream to marker rs6932056, making the total length of the risk haplotype approximately 109 kb.

effect (LRT P=0.554), while haplotype 3 did show an independent genetic effect (LRT P=0.0001). The inventors then asked the converse question of whether a genetic effect remained for one haplotype when the analysis was conditioned on the other haplotype. In line with the previous result, the detected significant residual genetic association when the analysis was conditioned on haplotype 2 (LRT $P=9.7\times10^{-5}$), while no genetic association remained when the inventors conditioned upon haplotype 3 (LRT P=0.422). They concluded that variants on Haplotype 3, the haplotype originally identified in the inventors' GWAS, are responsible for the association with SLE.

Thus, through imputation of this GWAS data with Phase II HapMap data in the region of TNFAIP3, the inventors identified an additional 11 variants that demonstrate association with SLE. All these SNPs, together with the three observed SNPs comprise a risk haplotype the extends approximately 109 kb in length, completely spanning TNFAIP3. While three common haplotypes are present in this EA population, conditional analysis supports only one haplotype driving the SLE association.

Predicting functional potential of SNPs on the TNFAIP3 risk haplotype. As discussed above, the inventors have described genetic association between variants in the region of TNFAIP3 with human SLE. This association effect is seen across multiple independent EA cohorts and, through imputation, appears to be localized to a 109 kb segment of tight LD ($r^2=1$) that spans the TNFAIP3 gene. While the strong LD in the region is helpful for localizing the effect in a genome-wide scan, it limits the ability to narrow the risk interval and

TABLE 3

Results of Imputation

| SNP | BP | NPRX | INFO | A1 | A2 | F_A | F_U | CHISQ | P | OR |
|---|---|---|---|---|---|---|---|---|---|---|
| rs10499197 | 138174209 | 3 | 1.01 | C | A | 0.06032 | 0.03016 | 19.25 | 1.15E−05 | 2.064 |
| rs9494883 | 138213159 | 4 | 1 | G | A | 0.06338 | 0.0298 | 23.52 | 1.24E−06 | 2.203 |
| rs9494885 | 138214441 | 4 | 0.737 | C | T | 0.1275 | 0.08372 | 15.19 | 9.72E−05 | 1.6 |
| rs11970411 | 138220854 | 5 | 1.02 | C | G | 0.1221 | 0.07741 | 18.28 | 1.91E−05 | 1.657 |
| rs9494886 | 138226023 | 5 | 1.02 | G | C | 0.1221 | 0.07741 | 18.28 | 1.91E−05 | 1.657 |
| rs3757173 | 138231847 | 5 | 1.02 | G | A | 0.1221 | 0.07741 | 18.28 | 1.91E−05 | 1.657 |
| rs719149 | 138234438 | 5 | 1.02 | A | G | 0.1221 | 0.07741 | 18.28 | 1.91E−05 | 1.657 |
| rs5029937 | 138236844 | 4 | 1 | T | G | 0.06338 | 0.0298 | 23.52 | 1.24E−06 | 2.203 |
| rs5029939 | 138237416 | 4 | 0.864 | C | G | 0.06961 | 0.03132 | 29.02 | 7.17E−08 | 2.314 |
| rs7752903 | 138269057 | 3 | 1.01 | G | T | 0.06148 | 0.02994 | 21.04 | 4.50E−06 | 2.122 |
| rs9494894 | 138270213 | 4 | 1 | C | T | 0.06338 | 0.0298 | 23.52 | 1.24E−06 | 2.203 |
| rs7749323 | 138272082 | 3 | 1 | T | C | 0.06148 | 0.02993 | 21.07 | 4.44E−06 | 2.123 |
| rs9494895 | 138276471 | 5 | 0.979 | T | C | 0.06118 | 0.02826 | 23.59 | 1.19E−06 | 2.241 |
| rs6932056 | 138284130 | 3 | 1.01 | C | T | 0.06148 | 0.02993 | 21.07 | 4.44E−06 | 2.123 |

Figure 6:
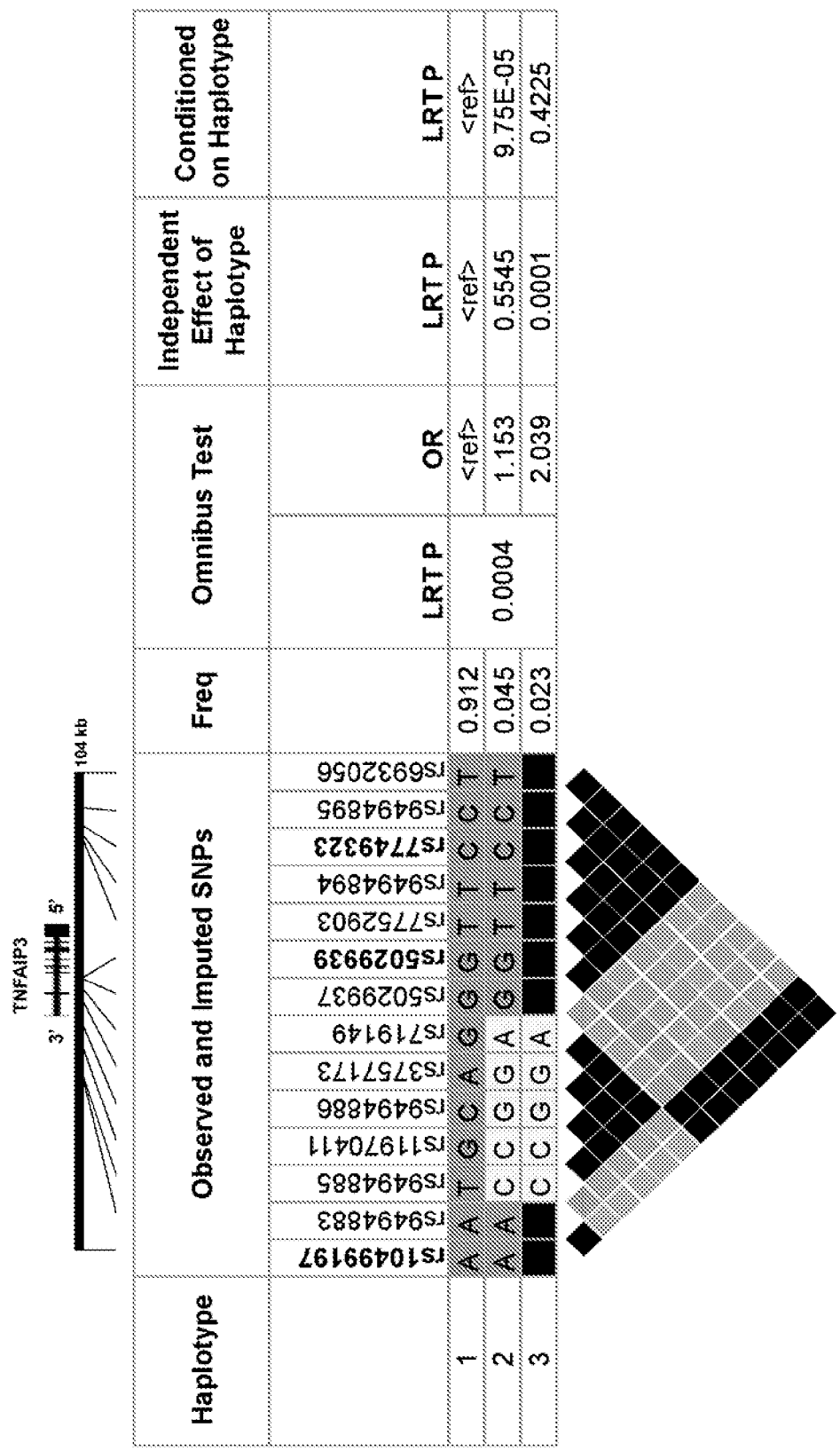
FIG. 6. Conditional haplotype analyses for the imputed TNFAIP3 risk haplotype. Three haplotypes are shown with frequencies >1%. Imputed SNPs and observed SNPs (bold) are shown. LD relationships ($r^2$) are shown in the figure below the table with black and gray squares corresponding to $r^2 = 0.95$-1.0 and 0.5-0.95, respectively. The approximate genomic location of each SNP in reference to TNFAIP3 is shown in the figure above the table. Analysis was performed using PLINK. LRT=likelihood ratio test.

NPRX - number of proxies SNPs used to impute
INFO - score of accuracy of imputation
A1/A2 - allele 1 or 2
F_A/F_U - allele frequency in affected/unaffected The haplotypic and LD relationships for the observed and imputed SNPs are shown in FIG. 6. Three haplotypes are identified with haplotypic frequency >1%. Within the haplotypes two primary haplotype blocks are noted, the first is marked by five SNPs and is carried on both haplotypes 2 and 3 (FIG. 6, yellow). The second LD block is specific for haplotype 3 (red) and marks the original risk haplotype discovered in the LuMNAS GWAS. The inventors used haplotypic conditional analysis to determine if the two blocks contributed independent genetic risk for SLE. As expected, the omnibus likelihood ratio test (LRT) showed a P-value=0.0004 suggesting that variants in the region of TNFAIP3 influence risk for SLE. They then asked whether either haplotype demonstrated an independent effect for association. The results showed that haplotype 2 did not contribute an independent identify the functional allele using genetic methods. In an attempt to address this issue, the inventors used a systematic bioinformatics approach to assess the potential for any of the 15 SNPs (including rs2230926, the exon 3 mis-sense SNP describe earlier) identified in the SLE risk haplotype to be functional. As a framework, they used the information provided from the SNPseek database (snp.wustl.edu/cgi-bin/SNPseek). SNPseek queries public resources and partitions SNPs based on alteration within a protein coding region (non-synonymous, splice site, exonic splice enhancer or silencer (ESE/ESS)), locality within a gene expression regulatory sequence (conserved transcription factor binding site, conserved regulatory sequence across 7 mammalian species, miRNA binding sites) or whether the SNP resides in an evolutionarily conserved domain. SNPseek also extracts population specific allele frequency information from the HapMap database for each SNP. In addition to this data, the inventors interrogated the ENSEMBL Gene Regulators in Disease (GRID) website for data pertaining to CpG islands, cis-regulatory modules (PreMOD) (Ferretti et al., 2007) and SNP associated transcript isoform expression (Kwan et al., 2008) and gene expression quantitative trait loci (eQTL) (Dixon et al., 2007). The result of this analysis is summarized in Table 4.

less efficient attenuation of NF-κB signaling (Musone et al., 2008). This SNP also resides in a putative exonic splice enhancer (ESE) sequence as determined by the ExonScan database (Wang et al., 2004). ESE and exonic splice silencers (ESS) are short redundant DNA sequences that facilitate the assembly of the "spliceosome" complex resulting in constitutive or alternative mRNA splicing (Wang et al., 2004). Whether rs2230926 actually influences alternative splicing of TNFAIP3 transcripts is not known. Not surprisingly given its

TABLE 4

Bioinformatic Assessment of Potential SNP Function

4A

| | Genomic Information | | | | HAPMAP Population Data | | | | | | | |
|---|---|---|---|---|---|---|---|---|---|---|---|---|
| | | | | | CEU | | YRI | | CHP | | JPT | |
| SNP | Position | Strand | Allele | Region | MAF | Allele | MAF | Allele | MAF | Allele | MAF | Allele |
| rs10499197 | 138174209 | + | G/T | Intergenic | 0.03 | G | 0.03 | G | 0.00 | G | 0.00 | G |
| rs9494883 | 138213159 | + | A/G | utr | 0.04 | G | 0.27 | G | 0.09 | G | 0.09 | G |
| rs9494885 | 138214441 | + | C/T | utr | 0.11 | C | 0.31 | T | 0.13 | C | 0.13 | C |
| rs11970411 | 138220854 | + | C/G | utr | 0.09 | C | 0.35 | G | 0.12 | C | 0.12 | C |
| rs9494886 | 138226023 | + | C/G | Intron | 0.08 | G | 0.39 | C | 0.13 | G | 0.13 | G |
| rs3757173 | 138231847 | − | C/T | utr | 0.09 | G | 0.33 | A | 0.11 | G | 0.11 | G |
| rs719149 | 138234438 | + | A/G | Intron | 0.09 | A | 0.37 | G | 0.11 | A | 0.11 | A |
| rs5029937 | 138236844 | − | G/T | Intron | 0.04 | T | 0.50 | T | 0.08 | T | 0.08 | T |
| rs5029939 | 138237416 | + | C/G | Intron | 0.04 | G | 0.50 | G | 0.08 | G | 0.08 | G |
| rs2230926 | 138237759 | + | G/T | Exon | 0.00 | G | 0.47 | T | 0.08 | G | 0.08 | G |
| rs7752903 | 138269057 | + | G/T | Intergenic | 0.02 | G | 0.05 | G | 0.08 | G | 0.08 | G |
| rs9494894 | 138270213 | + | C/T | Intergenic | 0.04 | C | 0.22 | C | 0.08 | C | 0.08 | C |
| rs7749323 | 138272082 | + | A/G | Intergenic | 0.03 | A | 0.05 | A | 0.08 | A | 0.08 | A |
| rs9494895 | 138276471 | + | C/T | Intergenic | 0.04 | T | 0.22 | T | 0.08 | T | 0.08 | T |
| rs6932056 | 138284130 | + | C/T | Intergenic | 0.03 | C | 0.05 | C | 0.09 | C | 0.09 | C |

4B

| | Protein Coding | | | | Expression | | | | | | Conserved | |
|---|---|---|---|---|---|---|---|---|---|---|---|---|
| SNP | NON SYN | SPLICE | ESE | ESS | TFBS CONS | CPG ISLAND | CRM | REG 7X | miRNA | eQTL | RODENT | VERTEBRATE |
| rs10499197 | | | | | | | X | X | | | | |
| rs9494883 | | | | | | | | | | | | |
| rs9494885 | | | | | | | | | | | | |
| rs11970411 | | | | | | | | | | | | |
| rs9494886 | | | | | | | | | | | | |
| rs3757173 | | | | | | | | | | | | |
| rs719149 | | | | | | | | | | | | |
| rs5029937 | | | | | | | | | | | | |
| rs5029939 | | | | | | | | X | | | | |
| rs2230926 | X | | X | | | | | X | | | | X |
| rs7752903 | | | | | | | | | | | | |
| rs9494894 | | | | | | | | | | | | |
| rs7749323 | | | | | | | | | | | | |
| rs9494895 | | | | | | | | | | | | |
| rs6932056 | | | | | | | | | | | | |

Figure 7:
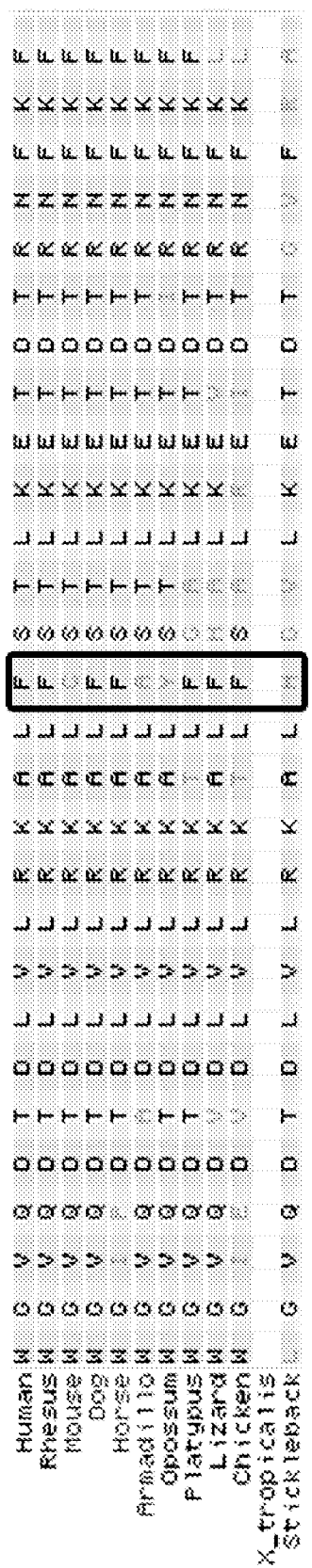
FIG. 7. Conservation of amino acid residues in exon 3 of TNFAIP3. Amino acid residue 127 encoded by a codon that includes rs2230926 is highlighted in the box. This residue is not particularly well conserved across species compared to neighboring residues (SEQ ID NOS: 3 through 13).
Figure 8:
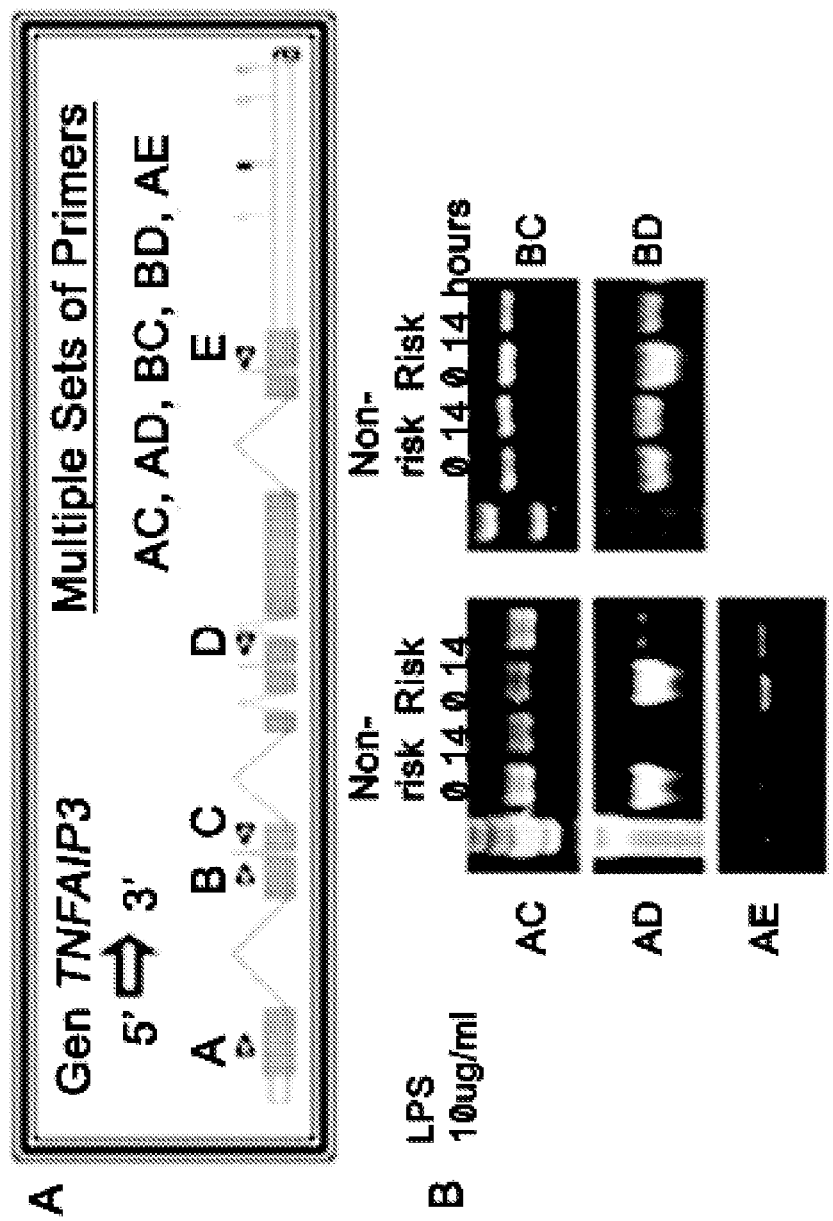
FIGS. 8A-B. Transcripts arising from the traditional promoter have no detectable splice variation independent of haplotype.

Abbreviations:
CEU = Ceph Utah individuals (European descent); YRI = Yoruba tribe individuals (African descent); CHB = Han Chinese of Beijing; JPT = Jananese of Tokyo; utr = untranslated region; non-synon = Nonsynonymous SNP that causes amino acid change; splice = splice donor/acceptor site; ese = putative exon splicing enhancer; ess = putative exon splicing silencer; tfbs cons = conserved transcription factor binding site; reg 7x = regulatory potentila region from 7 species alignment; CRM = cis-regulatory module from PreMod database (XXX); miRNA = miRNA binding site in 3' UTR; eQTL = expression quantitative trait locus; rodent = human-mouse-rat conserced region; vertebrate = human-17 vertebrqte conserved region For most of the SNPs on the risk haplotype, no data are available to support a role for any of the functional predictions the inventors evaluated (Table 4). SNPs rs5029939 and rs10499197 are located in regions of conserved regulatory potential across various mammalian species and rs10499197 is within a cis-regulatory module predicted by PreMOD that may influence gene expression (Ferretti et al., 2007). The most likely functional candidate at this point is rs2230926, the non-synonymous coding region SNP that results in a phenylalanine to cysteine substitution at position 127 (F127C) of A20. Preliminary evidence in non-lymphoid transfected cell lines suggests that the minor allele may result exon location, rs2230926 is located in a region of conservation with other species (Reg 7X and vertebrate conserved), however the amino acid 127, partially encoded by rs2230926, is not well conserved compared to neighboring residues suggesting that this residue may not be critical A20 function (FIG. 7). In support of this conclusion, PolyPhen (Ramensky et al., 2002), an algorithm that estimates the impact of non-synonymous coding SNPs on protein function, predicts the F127C substitution to be benign. Furthermore, the inventors' published data demonstrate that approximately ⅓ of chromosomes carrying the minor A allele of rs2230926 demonstrate no SLE association (Graham et al., 2008). While the coding SNP, rs2230926 remains an attractive functional candidate, the inventors cannot rule out the possibility that an untyped variant might also contribute to, or be responsible for, the association with SLE. Additional experiments are required to confirm that relevance of rs2230926 with SLE risk.

Experiments exploring functional mechanisms of SLE TNFAIP3 risk haplotype. The experiments that follow were performed with 2 independent cell lines for each of three possible genotypes determined by genotyping four SNPs that define the SLE risk haplotype (rs10499197, rs5029939, rs2230926, rs7749323). Stimulations were performed uniformly in all experiments with 10 ng/ml of the TLR4 agonist LPS or the receptor independent stimulus PMA (1 ng/ml) and Ionomycin (500 ng/ml) following overnight serum deprivation. Cells were harvested at various time points following stimulation as shown in FIGS. 8A-9D.

mRNA splicing events do not correlate with TNFAIP3 risk haplotype basally or following stimulation with agonists. To test the hypothesis that the TNFAIP3 risk haplotype influences mRNA splice variation, the inventors designed PCR primers that would interrogate all combinations of the major splice isoforms as defined by current EST databases. Cells homozygous for risk and non-risk haplotypes were stimulated in vitro with LPS or PMA/Ionomycin. Cells were harvested at specific time points, mRNA was purified and PCR performed using optimized protocols with the various primer sets shown in (FIG. 8A). While some isoforms appear relatively less abundant following stimulation (Primer set AD, FIG. 8B), the results show no specific splicing differences with any of the primer sets between risk and non-risk cells either at rest or up to 14 hours following LPS stimulation. Similar results were seen with PMA/Ionomycin (not shown). Experiments performed at earlier time points (1, 3, 6 hours) were similar to the 14-hour time point (not shown). From these data, the inventors conclude that with the current set of primers following stimulation with LPS or PMA/ionomycin no functional effect in mRNA splicing can be attributed to the TNFAIP3 risk haplotype up to 14 hours.

Figure 9A:
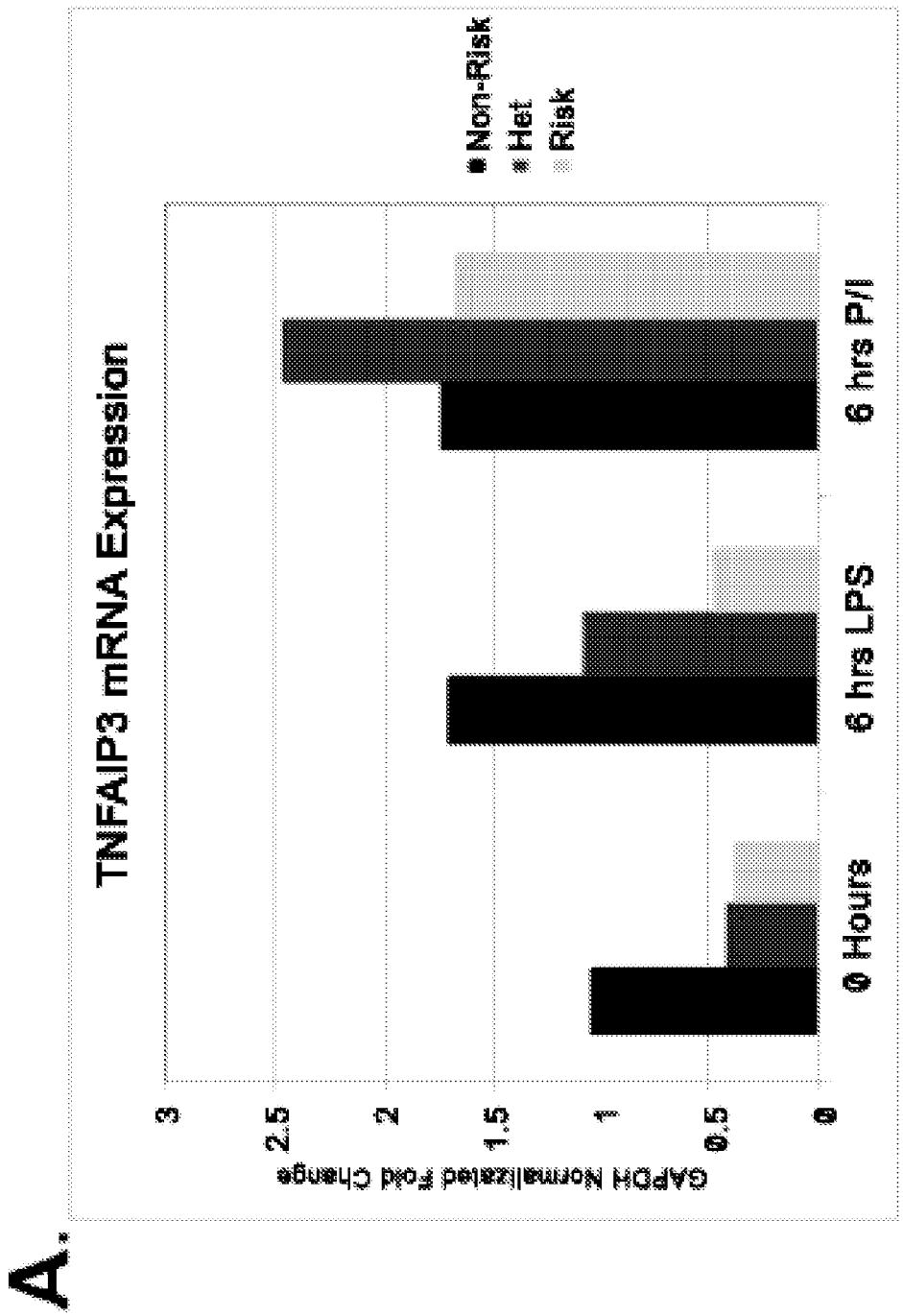
FIGS. 9A-D. EBV transformed lines carrying the TNFAIP3 risk haplotype demonstrate reduced expression of TNFAIP3 mRNA and protein, accumulate increased levels of intracellular TNFa and extracellular pro-inflammatory cytokines at rest or following TLR activation.

Cell lines carrying the TNFAIP3 risk haplotype demonstrate reduced expression of TNFAIP3 at rest and following TLR agonist stimulation. To determine if TNFAIP3 transcription and translation was influenced by the SLE associated risk haplotype, the inventors stimulated B cell lines with LPS and collected RNA and protein over time (FIG. 9A). Six-hours post-LPS produced maximal TNFAIP3 mRNA and that is what is shown in FIG. 9A. Quantitative PCR was performed using TNFAIP3 (target) and HPRT (calibrator) specific Taq-Man probes. Concentrations of each transcripts were determined using a standard dilution curve of plasmids containing each gene sequence. The results demonstrated that cell lines (N=2 for each genotype) carrying the risk haplotype expressed less TNFAIP3 at rest and produced less TNFAIP3 mRNA in response to LPS compared to non-risk lines. This reduced TNFAIP3 expression was, however, not due to the fact that the cells were incapable of expressing comparable levels TNFAIP3 transcripts as stimulation with PMA/ionomycin upregulated TNFAIP3 transcripts in all cell lines at levels that meet or exceed wild type cell lines (FIG. 9A).

Figure 9B:
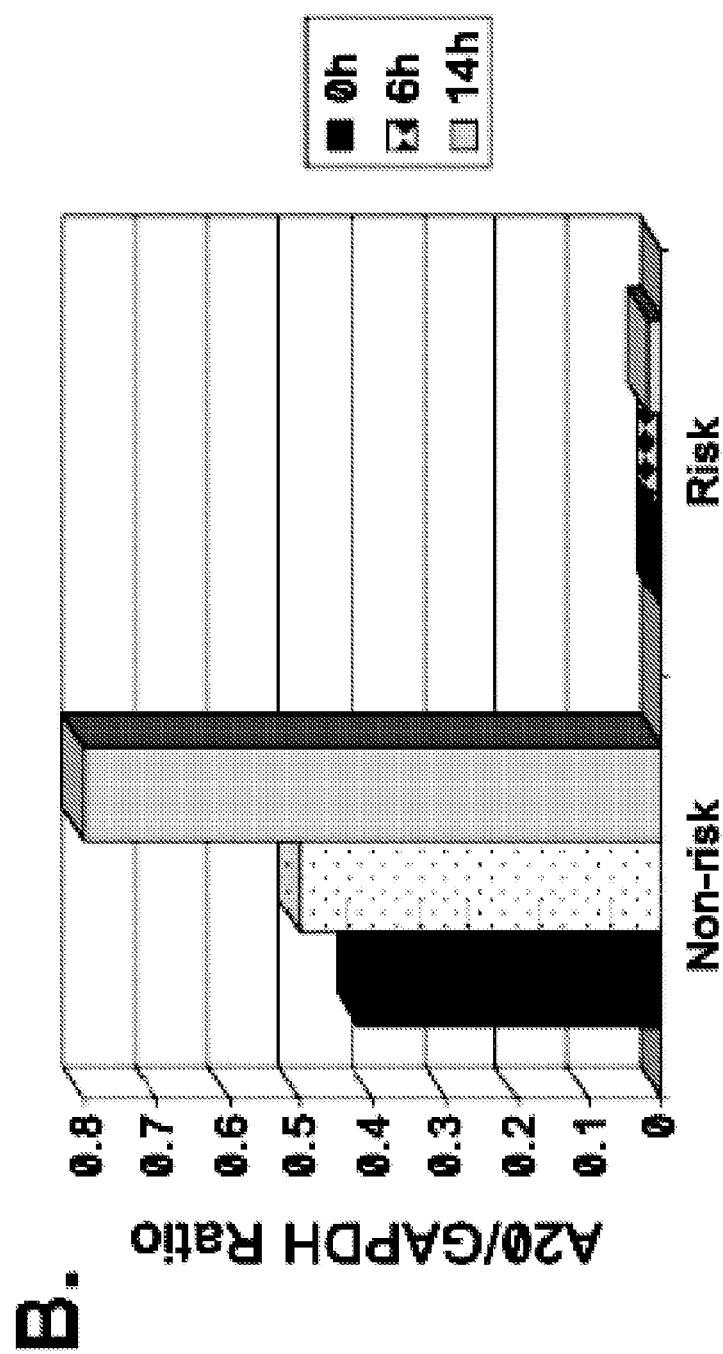

To determine if the TNFAIP3 risk haplotype also resulted in altered protein expression, the inventors stimulated the EBV-transformed B cell lines with LPS, harvested cell lysates, and performed western blot analysis for A20 protein followed by densitometry (FIG. 9B). This analysis demonstrates lower basal expression in homozygous risk lines (N=2) compared to homozygous non-risk lines (N=2). Following LPS stimulation risk cell lines demonstrate less time dependent upregulation of A20 compared with non-risk cell lines. These preliminary experiments to support the hypothesis that variants on the SLE risk haplotype result in decreased expression of TNFAIP3 basally and after stimulation with LPS.

Figure 9C:
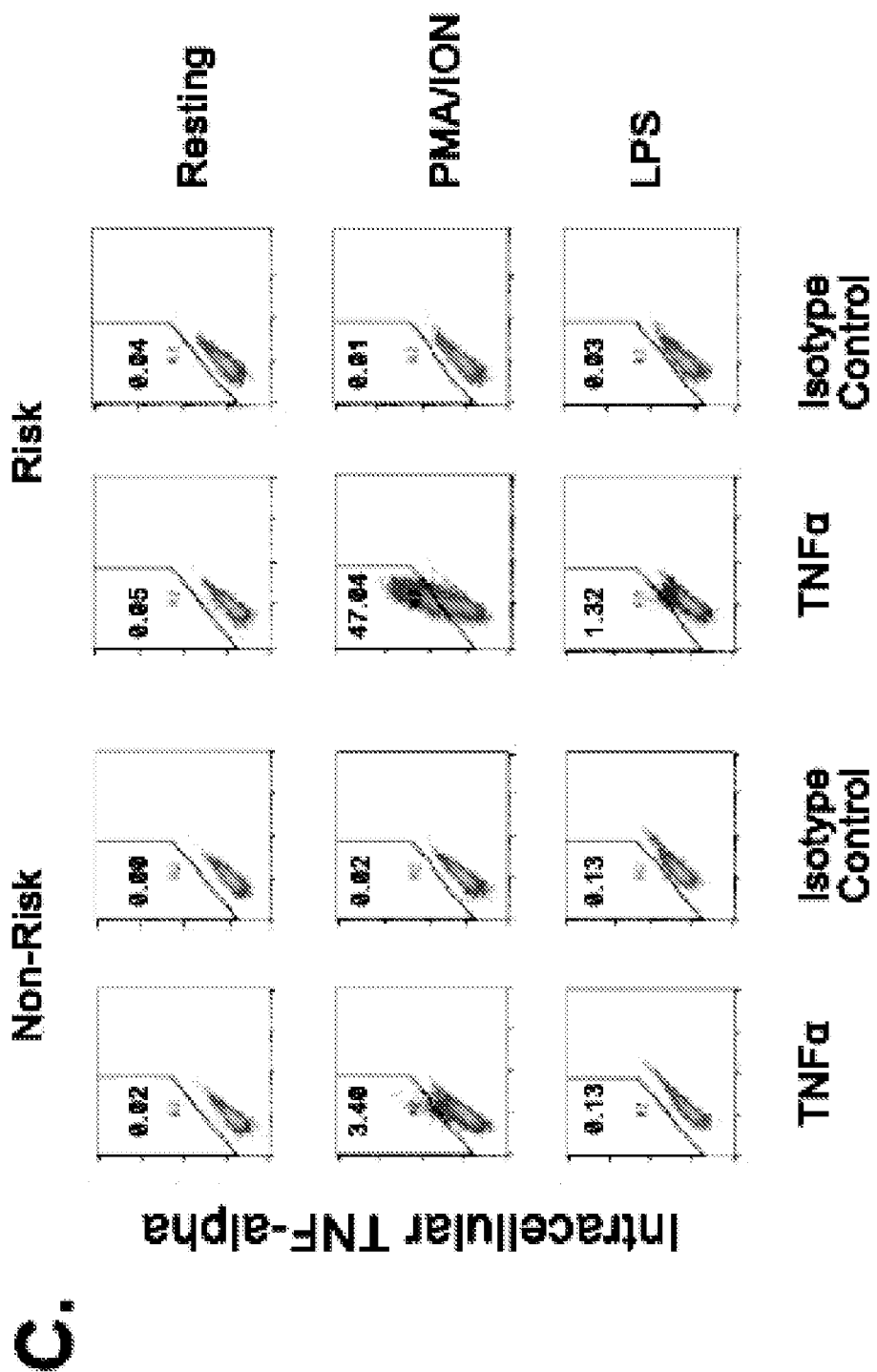
Figure 9D:
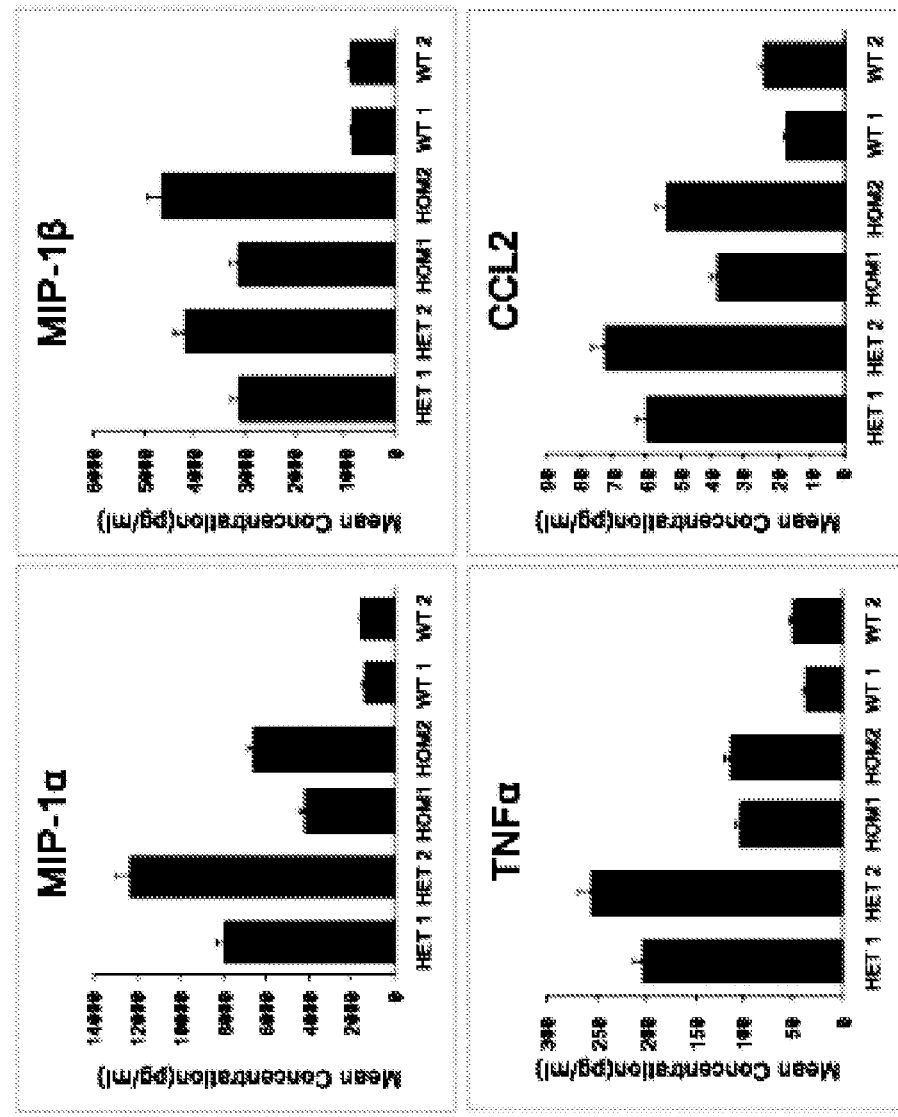

Cell lines carrying the TNFAIP3 risk haplotype demonstrate enhanced production of TNFα following TLR agonist stimulation and secrete greater amounts of proinflammatory cytokines at rest. Based on the previous results demonstrating lower expression of TNFAIP3 in cell lines carrying the risk haplotypes, the inventors postulated that this would result in enhanced expression of NF-κB dependent cytokines such as TNFα. To test this idea, homozygous cell lines expressing the risk and non-risk haplotypes (N=2) were stimulated with PMA/ionomycin or LPS as described above in the presence of monensin to block the extracellular secretion of TNFα. As predicted, the inventors found that risk haplotype lines accumulated approximately 10 times as much intracellular TNFα 14 hours after with PMA/ionomycin or LPS exposure compared with non-risk cell lines (FIG. 9C). They are re-evaluating the LPS dose and time course as the non-risk cells did not show an increase in TNFα; however, even at a dose that does not increase TNFα in non-risk cells, cells with the risk haplotype can be seen to accumulate TNFα, thus supporting the overall hypothesis. Furthermore, resting cell lines either heterozygous or homozygous for the TNFAIP3 risk haplotype secreted greater levels of the proinflammatory cytokines/chemokines TNFα, CCL2 (MCP-1), MIP-1a and MIP-1b into the media compared to WT cell lines when assayed by Luminex Bead assay (FIG. 9D). These results support the overall hypothesis that cells carrying the SLE risk associated haplotype have a defect in TNFAIP3 expression resulting in increased expression of NF-κB dependent proinflammatory cytokine/chemokine expression.

In summary, these preliminary data establish the strength and reproducibility of the TNFAIP3 association with SLE, define the boundaries of the associated DNA segment, suggest that none of the typed or imputed variants with the exception of the rs2230926 are likely to be causal, and thus provide support that unrecognized variants on the SLE risk haplotype result in reduced expression of TNFAIP3.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope, and concept of the invention as defined by the appended claims.

VII. References

The following references, to the extent that they provide exemplary procedural or other details supplementary to those set forth herein, are specifically incorporated herein by reference.

U.S. Pat. No. 4,659,774
U.S. Pat. No. 4,683,195
U.S. Pat. No. 4,683,202
U.S. Pat. No. 4,800,159

U.S. Pat. No. 4,816,571
U.S. Pat. No. 4,883,750
U.S. Pat. No. 4,959,463
U.S. Pat. No. 5,141,813
U.S. Pat. No. 5,242,974
U.S. Pat. No. 5,264,566
U.S. Pat. No. 5,384,261
U.S. Pat. No. 5,405,783
U.S. Pat. No. 5,412,087
U.S. Pat. No. 5,424,186
U.S. Pat. No. 5,428,148
U.S. Pat. No. 5,429,807
U.S. Pat. No. 5,436,327
U.S. Pat. No. 5,445,934
U.S. Pat. No. 5,472,672
U.S. Pat. No. 5,527,681
U.S. Pat. No. 5,529,756
U.S. Pat. No. 5,532,128
U.S. Pat. No. 5,545,531
U.S. Pat. No. 5,554,501
U.S. Pat. No. 5,554,744
U.S. Pat. No. 5,556,752
U.S. Pat. No. 5,561,071
U.S. Pat. No. 5,571,639
U.S. Pat. No. 5,574,146
U.S. Pat. No. 5,593,839
U.S. Pat. No. 5,599,695
U.S. Pat. No. 5,602,244
U.S. Pat. No. 5,624,711
U.S. Pat. No. 5,658,734
U.S. Pat. No. 5,700,637
U.S. Pat. No. 5,757,994
U.S. Pat. No. 5,788,166
U.S. Pat. No. 5,838,002
U.S. Pat. No. 5,840,873
U.S. Pat. No. 5,843,640
U.S. Pat. No. 5,843,650
U.S. Pat. No. 5,843,651
U.S. Pat. No. 5,843,663
U.S. Pat. No. 5,846,708
U.S. Pat. No. 5,846,709
U.S. Pat. No. 5,846,717
U.S. Pat. No. 5,846,726
U.S. Pat. No. 5,846,729
U.S. Pat. No. 5,846,783
U.S. Pat. No. 5,849,481
U.S. Pat. No. 5,849,486
U.S. Pat. No. 5,849,487
U.S. Pat. No. 5,849,497
U.S. Pat. No. 5,849,546
U.S. Pat. No. 5,849,547
U.S. Pat. No. 5,851,772
U.S. Pat. No. 5,853,990
U.S. Pat. No. 5,853,992
U.S. Pat. No. 5,853,993
U.S. Pat. No. 5,856,092
U.S. Pat. No. 5,858,652
U.S. Pat. No. 5,861,244
U.S. Pat. No. 5,863,732
U.S. Pat. No. 5,863,753
U.S. Pat. No. 5,866,331
U.S. Pat. No. 5,866,366
U.S. Pat. No. 5,882,864
U.S. Pat. No. 5,900,481
U.S. Pat. No. 5,905,024
U.S. Pat. No. 5,910,407
U.S. Pat. No. 5,912,124
U.S. Pat. No. 5,912,145
U.S. Pat. No. 5,912,148
U.S. Pat. No. 5,916,776
U.S. Pat. No. 5,916,779
U.S. Pat. No. 5,919,626
U.S. Pat. No. 5,919,630
U.S. Pat. No. 5,922,574
U.S. Pat. No. 5,925,517
U.S. Pat. No. 5,928,862
U.S. Pat. No. 5,928,869
U.S. Pat. No. 5,928,905
U.S. Pat. No. 5,928,906
U.S. Pat. No. 5,929,227
U.S. Pat. No. 5,932,413
U.S. Pat. No. 5,932,451
U.S. Pat. No. 5,935,791
U.S. Pat. No. 5,935,825
U.S. Pat. No. 5,939,291
U.S. Pat. No. 5,942,391
U.S. Pat. No. 5,986,258
U.S. Pat. No. 6,004,755
U.S. Ser. No. 10/407,846
U.S. Pat. RE 35,413
Arend and Dayer, *Arthritis Rheum.*, 38:151-160, 1995.
Arnett et al., *Rheumatic Diseases Clinics of North America*, 18:865-92, 1992.
Baechler et al., *Proc. Natl. Acad. Sci. USA*, 100(5):2610-15, 2003.
Bahr et al., *J Mass Spectrom.*, 32:1111-1116, 1997.
Baichwal and Baeuerle, *Adv. Immunol.*, 65:111-137, 1997.
Bentzley et al., *Anal Chem.*, 68(13):2141-2146, 1996.
Boone et al., *Nat. Immunol.*, 5(10):1052-1060, 2004.
Bucknall et al., *J. Am. Soc. Mass Spectrom.*, 13(9):1015-1027, 2002.
Burger and Dayer, *Neurology*, 45(6S-6):S39-43, 1995.
Caprioli et al., *Anal. Chem.*, 69:4751, 1997.
Chaurand et al., *Anal Chem.*, 71(23):5263-5270, 1999.
Chen et al., *Nat. Biotechnol.*, 19:537-542, 2001.
Desiderio et al., *J Mass Spectrom.*, 35(6):725-733, 2000.
Desiderio et al., *Methods Mol. Biol.*, 61:57-65, 1996.
Dinarello, *Int. Rev. Immunol.*, 16:457-499, 1998.
Duncan et al., *Rapid Commun. Mass Spectrom.*, 7(12):1090-1094, 1993.
Durkop et al., *J. Pathol.*, 200(2):229-239, 2003.
Eastgate et al., *Lancet*, 2:706-709, 1988.
European Appln No. 320 308
European Appln. No. 329 822
Faulstich et al., *Anal. Chem.*, 69(21):4349-4353, 1997.
Fenn et al., *Science*, 246(4926):64-71, 1989.
Firestein et al., *Arthritis Rheum.*, 37:644-652, 1994.
Frohman, In: *PCR Protocols: A Guide To Methods And Applications*, Academic Press, N.Y., 1990.
Fujikawa et al., *Ann. Rheum. Dis.*, 54:318-320, 1995.
Gaffney et al., *Am. J. Hum. Genet.*, 66(2):547-556, 2000.
Gaffney et al., *Am. J. Hum. Genet.*, 78(5):747-758, 2006.
Gaffney et al., *Proc. Natl. Acad. Sci. USA*, 95: 14875-79, 1998.
GB Appln. No. 2 202 328
Gillam et al., *J. Biol. Chem.*, 253(8):2532-2539, 1978.
Gobom et al., *Anal. Chem.*, 72(14):3320-3326, 2000.
Graham et al., *Hum. Mol. Genet.*, 15(21):3195-3205, 2006.
Grey et al., *J Immunol.*, 170(12):6250-6256, 2003.
Grey et al., *J. Exp. Med.*, 190(8):1135-1146, 1999.
Guilfoyle et al., *Nucleic Acids Research*, 25:1854-1858, 1997.
Hannum et al., *Nature*, 343:336-340, 1990.

Harley et al., *Current Opinions in Immunology*, 10:690-96, 1998.
He and Ting, *Mol. Cell Biol.*, 22(17):6034-6045, 2002.
Hiramoto et al., *Oncogene*, 18(22):3422-3426, 1999.
Horak et al., *Rapid Commun. Mass Spectrom.*, 15(4):241-248, 2001.
Innis et al., *Proc. Natl. Acad. Sci. USA*, 85(24):9436-9440, 1988.
Itakura et al., *J. Am. Chem. Soc.*, 97(25):7327-7332, 1975.
Jarvis et al., *J. Virol.*, 80(11):5588-5598, 2006.
Jespersen et al., *Anal Chem.*, 71(3):660-666, 1999.
Jiang et al., *J. Agric. Food Chem.*, 48:3305, 2000.
Jonsson and Brokstad, In: *A Textbook of Rheumatology*, 6th Ed., Philadelphia, Lippincott Williams & Wilkins, 495-504, 2001.
Jonsson et al., *Br. J. Rheumatol.*, 32(7):578-581, 1993.
Jonsson et al., *Oral Dis.*, 8:130-140, 2002.
Kabarle et al., *Anal. Chem.* 65(20):972A-986A, 1993.
Kahle et al., *Ann. Rheum. Dis.*, 51:731-734, 1992.
Kanazawa et al., *Biol. Pharm. Bull.*, 22(4):339-346, 1999.
Kazmaier et al., *Anesthesiology*, 89(4):831-817, 1998.
Khorana, *Science*, 203(4381):614-625, 1979.
Kuehn, *JAMA*, 293:1315, 2005.
Kwoh et al., *Proc. Natl. Acad. Sci. USA*, 86: 1173, 1989.
Li et al., *Trends Biotechnol.*, 18:151, 2000.
Lipsky, In: *Harrison's principles of internal medicine*, Fauci et al. (Eds.), 14th Ed., NY, McGraw-Hill, 1880-1888, 1998.
Liuwantara et al., *Diabetes*, 55(9):2491-501, 2006.
Lynn et al., *J. Mol. Evol.*, 48(5):605-614, 1999.
Marie et al., *Anal. Chem.*, 72(20):5106-5114, 2000.
Miketova et al., *Mol. Biotechnol.*, 8(3):249-253, 1997.
Moser et al., *Proc. Natl. Acad. Sci. USA*, 95:14869-74, 1998.
Muddiman et al., *Fres. J. Anal. Chem.*, 354:103, 1996.
Nelson et al., *Anal. Chem.*, 66:1408, 1994.
Nguyen et al., *J. Chromatogr. A.*, 705(1):21-45, 1995.
Ohara et al., *Proc. Natl. Acad. Sci. USA*, 86: 5673-5677, 1989.
PCT Appln. PCT/US87/00880
PCT Appln. PCT/US89/01025
PCT Appln. WO 88/10315
PCT Appln. WO 89/06700
PCT Appln. WO 89/06700
PCT Appln. WO 90/07641
Prieur et al., *Lancet.*, 2:1240-1242, 1987.
Roepstorff, *EXS.*, 88:81-97, 2000.
Rooney et al., *Rheumatol. Int.*, 10:217-219, 1990.
Salomonsson et al., *Arthritis Rheum.*, 48:3187-201, 2003.
Salomonsson et al., *Scand J. Immunol.*, 55: 336-342, 2002.
Sambrook et al., In: *Molecular cloning*, Cold Spring Harbor Laboratory Press, Cold Spring Harbor, N.Y., 1989.
Stoeckli et al., *Nat. Med.*, 7(4):493-496, 2001.
Takach et al., *J. Protein Chem.*, 16:363, 1997.
van den Berg, *Semin. Arthritis Rheum.*, 30(5S-2):7-16, 2001.
Villanueva et al., *Enzyme Microb. Technol.*, 29:99, 1999.
Wakeland et al., *Immunity*, 15:690-96, 2001.
Walker et al., *Proc. Natl. Acad. Sci. USA*, 89:392-396 1992.
Wang et al., *Anal. Chem.*, 72(21):5285-5289, 2000.
Wang et al., *J. Agric. Food. Chem.*, 47:1549, 1999.
Wang et al., *J. Agric. Food. Chem.*, 47:2009, 1999.
Wertz et al., *Nature*, 430(7000):694-699, 2004.
Weyand and Goronzy, *Ann. NY Acad. Sci.*, 987:140-149, 2003.
Wittmann et al., *Biotechnol. Bioeng.*, 72:642, 2001.
Wu et al., *Anal. Chem.*, 70:456A, 1998.
Wu et al., *Biochem. Biophys. Res. Commun.*, 233(1):221-226, 1997.
Wu et al., *Biochim. Biophys. Acta*, 1466:315-327, 2000.
Xanthou et al., *Arthritis Rheum.*, 44:408-418, 2001.
Yang et al., *J. Agric. Food. Chem.*, 48:3990, 2000.
Zhong et al., *Clin. Chem. ACTA.*, 313:147, 2001.
Zweigenbaum et al., *Anal. Chem.*, 71(13):2294-300, 1999.
Zweigenbaum et al., *J. Pharm. Biomed. Anal.*, 23(4):723-733, 2000.
Graham et al., *Nat. Genet.*, 2008. [Epub ahead of print]
Marchini et al., *Nat. Genet.*, 39(7):906-913, 2007.
Beyaert et al., *Biochem. Pharmacol.*, 60(8):1143-1151, 2000.
Harley et al., *Nat. Genet.*, 40(2):204-210, 2008.
Dixon et al., *Nat. Genet.*, 39(10):1202-1207, 2007.
Musone et al., *Nat. Genet.*, 2008. [Epub ahead of print]
Ramensky et al., *Nucleic Acids Res.*, 30(17):3894-3900, 2002.
Lee et al., *Science*, 289(5488):2350-2354, 2000.
Fisher, In: *Statistical Methods for Research Workers*, 13th Ed., London: Oliver and Lloyd, Ltd., 1925.
Ferretti et al., *Nucleic Acids Res.*, 35:D122-D126, 2007.
Kwan et al., *Nat. Genet.*, 40(2):225-231, 2008.
Wang et al., *Cell*, 119(6):831-845, 2004.
Mirgorodskaya et al., *Rapid Commun. Mass Spectrom.*, 14(14):1226-1232, 2000.
Song et al., *Proc. Natl. Acad. Sci. USA*, 93(13):6721-5, 1996.
Heyninck et al., *J Cell Biol.* 1999 Jun. 28; 145(7):1471-82, 1999.
Grey et al., *Transplant Proc.*, 33(1-2):577-8, 2001.
Heyninck and Beyaert, *Trends Biochem. Sci.*, 30(1):1-4, 2005.
Lovelace et al., *J. Chromatogr.*, 562(1-2):573-584, 1991.
Heyninck and Beyaert, *FEBS Lett.*, 442(2-3):147-150, 1999.
Arend et al., *Annu. Rev. Immunol.*, 16:27-55, 1998.
Beaucage, *Methods Mol. Biol.*, 20:33-61, 1993.

---

What is claimed is:

1. A method of identifying an increased risk of developing systemic lupus erythematosus (SLE) in a human subject comprising:
   (a) obtaining a nucleic acid-containing sample from said subject;
   (b) determining the presence in the sample of an A allele at rs7749323 in a tumor necrosis factor, alpha-induced protein 3 (TNFAIP3) gene, wherein the presence of the A allele at rs7749323 indicates an increased risk for SLE in the subject.

2. The method of claim 1 further comprising determining the presence or absence of an allele at rs10499197, rs3757173, rs629953, rs5029939, rs2230926 or combination thereof.

3. The method of claim 1 further comprising determining the presence or absence of an allele at rs10499197, rs3757173, rs629953, rs5029939, and rs2230926.

4. The method of claim 1, further comprising treating said subject based on the results of step (b).

5. The method of claim 1, further comprising taking a clinical history from said subject.

6. The method of claim 1, wherein determining comprises nucleic acid amplification.

7. The method of claim 6, wherein amplification comprises PCR.

8. The method of claim 1, wherein determining comprises primer extension.

9. The method of claim 1, wherein determining comprises restriction digestion.

10. The method of claim 1, wherein determining comprises sequencing.

11. The method of claim 1, wherein determining comprises SNP specific oligonucleotide hybridization.

12. The method of claim 1, wherein determining comprises a DNAse protection assay.

13. The method of claim 1, wherein said sample is blood, sputum, saliva, mucosal scraping or tissue biopsy.

* * * * *

UNITED STATES PATENT AND TRADEMARK OFFICE
CERTIFICATE OF CORRECTION

| | | |
|---|---|---|
| PATENT NO. | : 8,008,013 B2 | Page 1 of 1 |
| APPLICATION NO. | : 12/272265 | |
| DATED | : August 30, 2011 | |
| INVENTOR(S) | : Gaffney et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 80 days.

Signed and Sealed this
Thirty-first Day of January, 2012

David J. Kappos
*Director of the United States Patent and Trademark Office*

SEQUENCE LISTING

<160> NUMBER OF SEQ ID NOS: 13

<210> SEQ ID NO 1
<211> LENGTH: 4446
<212> TYPE: DNA
<213> ORGANISM: Homo sapiens

<400> SEQUENCE: 1

```
tgccttgacc aggacttggg actttgcgaa aggatcgcgg ggcccggaga ggtgttggag      60
agcacaatgg ctgaacaagt ccttcctcag gctttgtatt tgagcaatat gcggaaagct     120
gtgaagatac gggagagaac tccagaagac atttttaaac ctactaatgg gatcattcat     180
```

```
cattttaaaa ccatgcaccg atacacactg gaaatgttca gaacttgcca gttttgtcct    240
cagtttcggg agatcatcca caaagccctc atcgacagaa acatccaggc caccctggaa    300
agccagaaga aactcaactg gtgtcgagaa gtccggaagc ttgtggcgct gaaaacgaac    360
ggtgacggca attgcctcat gcatgccact tctcagtaca tgtggggcgt tcaggacaca    420
gacttggtac tgaggaaggc gctgttcagc acgctcaagg aaacagacac acgcaacttt    480
aaattccgct ggcaactgga gtctctcaaa tctcaggaat tgttgaaaac ggggcttgc     540 tatgatactc ggaactggaa tgatgaatgg gacaatctta tcaaaatggc ttccacagac    600
acacccatgg cccgaagtgg acttcagtac aactcactgg aagaaataca catatttgtc    660
ctttgcaaca tcctcagaag gccaatcatt gtcatttcag acaaaatgct aagaagtttg    720
gaatcaggtt ccaatttcgc ccctttgaaa gtgggtggaa tttacttgcc tctccactgg    780
cctgcccagg aatgctacag ataccccatt gttctcggct atgacagcca tcattttgta    840
cccttggtga ccctgaagga cagtgggcct gaaatccgag ctgttccact tgttaacaga    900
gaccggggaa gatttgaaga cttaaaagtt cactttttga cagatcctga aaatgagatg    960
aaggagaagc tcttaaaaga gtacttaatg gtgatagaaa tccccgtcca aggctgggac   1020
catggcacaa ctcatctcat caatgccgca aagttggatg aagctaactt accaaaagaa   1080
atcaatctgg tagatgatta ctttgaactt gttcagcatg agtacaagaa atggcaggaa   1140
aacagcgagc aggggaggag agaggggcac gcccagaatc ccatggaacc ttccgtgccc   1200
cagctttctc tcatggatgt aaaatgtgaa acgcccaact gcccctttt catgtctgtg    1260 aacacccagc ctttatgcca tgagtgctca gagaggcggc aaaagaatca aaacaaactc   1320
ccaaagctga actccaagcc gggccctgag gggctccctg gcatggcgct cggggcctct   1380
cggggagaag cctatgagcc cttggcgtgg aaccctgagt agtccactgg ggggcctcat   1440
tcggccccac cgacagcacc cagccctttt ctgttcagtg agaccactgc catgaagtgc   1500
aggagccccg gctgccccttt cacactgaat gtgcagcaca acggattttg tgaacgttgc   1560
cacaacgccc ggcaacttca cgccagccac gccccagacc acacaaggca cttggatccc   1620
gggaagtgcc aagcctgcct ccaggatgtt accaggacat ttaatgggat ctgcagtact   1680
tgcttcaaaa ggactacagc agaggcctcc tccagcctca gcaccagcct ccctccttcc   1740
tgtcaccagc gttccaagtc agatccctcg cggctcgtcc ggagcccctc cccgcattct   1800
tgccacagag ctggaaacga cgcccctgct ggctgcctgt ctcaagctgc acggactcct   1860
ggggacagga cggggacgag caagtgcaga aaagccggct gcgtgtattt tgggactcca   1920
gaaaacaagg gcttttgcac actgtgtttc atcgagtaca gagaaaacaa acattttgct   1980
gctgcctcag ggaaagtcag tcccacagcg tccaggttcc agaacaccat tccgtgcctg   2040
gggagggaat gcggcaccct tggaagcacc atgtttgaag gatactgcca gaagtgtttc   2100
attgaagctc agaatcagag atttcatgag gccaaaagga cagaagagca actgagatcg   2160
agccagcgca gagatgtgcc tcgaaccaca caaagcacct caaggcccaa gtgcgcccgg   2220
gcctcctgca gaacatcct ggcctgccgc agcgaggagc tctgcatgga gtgtcagcat   2280
cccaaccaga ggatgggccc tggggcccac cggggtgagc ctgcccccga agacccccccc  2340 aagcagcgtt gccgggcccc cgcctgtgat cattttggca atgccaagtg caacggctac   2400
tgcaacgaat gctttcagtt caagcagatg tatggctaac cggaaacagg tgggtcacct   2460
cctgcaagaa gtgggcctc gagctgtcag tcatcatggt gctatcctct gaaccctca   2520 gctgccactg caacagtggg cttaagggtg tctgagcagg agaggaaga taagctcttc   2580
```

```
gtggtgccca cgatgctcag gtttggtaac ccgggagtgt tcccaggtgg ccttagaaag    2640
caaagcttgt aactggcaag ggatgatgtc agattcagcc caaggttcct cctctcctac    2700
caagcaggag gccaggaact tctttggact tggaaggtgt gcggggactg gccgaggccc    2760
ctgcaccctg cgcatcagga ctgcttcatc gtcttggctg agaaagggaa aagcacaca    2820
agtcgcgtgg gttggagaag ccagagccat tccacctccc ctcccccagc atctctcaga    2880
gatgtgaagc cagatcctca tggcagcgag gccctctgca agaagctcaa ggaagctcag    2940
ggaaaatgga cgtattcaga gagtgtttgt agttcatggt ttttccctac ctgcccggtt    3000
cctttcctga ggacccggca gaaatgcaga accatccatg gactgtgatt ctgaggctgc    3060
tgagactgaa catgttcaca ttgacagaaa acaagctgc tctttataat atgcaccttt    3120
taaaaaatta gaatatttta ctgggaagac gtgtaactct ttgggttatt actgtcttta    3180
cttctaaaga agttagcttg aactgaggag taaaagtgtg tacatatata atataccctt    3240
acattatgta tgagggattt ttttaaatta tattgaaatg ctgccctaga agtacaatag    3300
gaaggctaaa taataataac ctgttttctg gttgttgttg gggcatgagc ttgtgtatac    3360
actgcttgca taaactcaac cagctgcctt tttaaaggga gctctagtcc ttttgtgta    3420
attcacttta tttattttat tacaaacttc aagattattt aagtgaagat atttcttcag    3480
ctctggggaa aatgccacag tgttctcctg agagaacatc cttgctttga gtcaggctgt    3540
gggcaagttc ctgaccacag ggagtaaatt ggcctctttg atacactttt gcttgcctcc    3600
ccaggaaaga aggaattgca tccaaggtat acatacatat tcatcgatgt ttcgtgcttc    3660
tccttatgaa actccagcta tgtaataaaa aactatactc tgtgttctgt taatgcctct    3720
gagtgtccta cctccttgga gatgagatag ggaaggagca gggatgagac tggcaatggt    3780
cacagggaaa gatgtggcct tttgtgatgg ttttattttc tgttaacact gtgtcctggg    3840
ggggctggga agtcccctgc atcccatggt accctggtat tgggacagca aaagccagta    3900
accatgagta tgaggaaatc tctttctgtt gctggcttac agtttctctg tgtgctttgt    3960
ggttgctgtc atatttgctc tagaagaaaa aaaaaaagg aggggaaatg catttttccc    4020
agagataaag gctgccattt tggggtctg tacttatggc ctgaaaatat ttgtgatcca    4080
taactctaca cagcctttac tcatactatt aggcacactt tccccttaga gcccctaag    4140
tttttcccag acgaatcttt ataatttctt tccaaagata ccaaataaac ttcagtgttt    4200
tcatctaatt ctcttaaagt tgatatctta atattttgtg ttgatcatta tttccattct    4260
taatgtgaaa aaaagtaatt atttatactt attataaaaa gtatttgaaa tttgcacatt    4320
taattgtccc taatagaaag ccacctattc tttgttggat ttcttcaagt ttttctaaat    4380
aaatgtaact tttcacaaga gtcaacatta aaaaataaat tatttaagaa caaaaaaaaa    4440
aaaaaa                                                                4446
```

<210> SEQ ID NO 2
<211> LENGTH: 790
<212> TYPE: PRT
<213> ORGANISM: Homo sapiens

<400> SEQUENCE: 2

```
Met Ala Glu Gln Val Leu Pro Gln Ala Leu Tyr Leu Ser Asn Met Arg
1               5                   10                  15

Lys Ala Val Lys Ile Arg Glu Arg Thr Pro Glu Asp Ile Phe Lys Pro
            20                  25                  30

Thr Asn Gly Ile Ile His His Phe Lys Thr Met His Arg Tyr Thr Leu
        35                  40                  45
```

-continued

```
Glu Met Phe Arg Thr Cys Gln Phe Cys Pro Gln Phe Arg Glu Ile Ile
 50                  55                  60

His Lys Ala Leu Ile Asp Arg Asn Ile Gln Ala Thr Leu Glu Ser Gln
 65                  70                  75                  80

Lys Lys Leu Asn Trp Cys Arg Glu Val Arg Lys Leu Val Ala Leu Lys
                 85                  90                  95

Thr Asn Gly Asp Gly Asn Cys Leu Met His Ala Thr Ser Gln Tyr Met
            100                 105                 110

Trp Gly Val Gln Asp Thr Asp Leu Val Leu Arg Lys Ala Leu Phe Ser
            115                 120                 125

Thr Leu Lys Glu Thr Asp Thr Arg Asn Phe Lys Phe Arg Trp Gln Leu
130                 135                 140

Glu Ser Leu Lys Ser Gln Glu Phe Val Glu Thr Gly Leu Cys Tyr Asp
145                 150                 155                 160

Thr Arg Asn Trp Asn Asp Glu Trp Asp Asn Leu Ile Lys Met Ala Ser
                165                 170                 175

Thr Asp Thr Pro Met Ala Arg Ser Gly Leu Gln Tyr Asn Ser Leu Glu
            180                 185                 190

Glu Ile His Ile Phe Val Leu Cys Asn Ile Leu Arg Arg Pro Ile Ile
            195                 200                 205

Val Ile Ser Asp Lys Met Leu Arg Ser Leu Glu Ser Gly Ser Asn Phe
210                 215                 220

Ala Pro Leu Lys Val Gly Gly Ile Tyr Leu Pro Leu His Trp Pro Ala
225                 230                 235                 240

Gln Glu Cys Tyr Arg Tyr Pro Ile Val Leu Gly Tyr Asp Ser His His
                245                 250                 255

Phe Val Pro Leu Val Thr Leu Lys Asp Ser Gly Pro Glu Ile Arg Ala
            260                 265                 270

Val Pro Leu Val Asn Arg Asp Arg Gly Arg Phe Glu Asp Leu Lys Val
            275                 280                 285

His Phe Leu Thr Asp Pro Glu Asn Glu Met Lys Glu Lys Leu Leu Lys
290                 295                 300

Glu Tyr Leu Met Val Ile Glu Ile Pro Val Gln Gly Trp Asp His Gly
305                 310                 315                 320

Thr Thr His Leu Ile Asn Ala Ala Lys Leu Asp Glu Ala Asn Leu Pro
                325                 330                 335

Lys Glu Ile Asn Leu Val Asp Asp Tyr Phe Glu Leu Val Gln His Glu
            340                 345                 350

Tyr Lys Lys Trp Gln Glu Asn Ser Glu Gln Gly Arg Arg Glu Gly His
            355                 360                 365

Ala Gln Asn Pro Met Glu Pro Ser Val Pro Gln Leu Ser Leu Met Asp
370                 375                 380

Val Lys Cys Glu Thr Pro Asn Cys Pro Phe Phe Met Ser Val Asn Thr
385                 390                 395                 400

Gln Pro Leu Cys His Glu Cys Ser Glu Arg Arg Gln Lys Asn Gln Asn
                405                 410                 415

Lys Leu Pro Lys Leu Asn Ser Lys Pro Gly Pro Glu Gly Leu Pro Gly
            420                 425                 430

Met Ala Leu Gly Ala Ser Arg Gly Glu Ala Tyr Glu Pro Leu Ala Trp
            435                 440                 445

Asn Pro Glu Glu Ser Thr Gly Gly Pro His Ser Ala Pro Pro Thr Ala
450                 455                 460

Pro Ser Pro Phe Leu Phe Ser Glu Thr Thr Ala Met Lys Cys Arg Ser
```

```
                465                 470                 475                 480
        Pro Gly Cys Pro Phe Thr Leu Asn Val Gln His Asn Gly Phe Cys Glu
                        485                 490                 495

Arg Cys His Asn Ala Arg Gln Leu His Ala Ser His Ala Pro Asp His
                        500                 505                 510

Thr Arg His Leu Asp Pro Gly Lys Cys Gln Ala Cys Leu Gln Asp Val
                        515                 520                 525

Thr Arg Thr Phe Asn Gly Ile Cys Ser Thr Cys Phe Lys Arg Thr Thr
                        530                 535                 540

Ala Glu Ala Ser Ser Ser Leu Ser Thr Ser Leu Pro Pro Ser Cys His
        545                 550                 555                 560

Gln Arg Ser Lys Ser Asp Pro Ser Arg Leu Val Arg Ser Pro Ser Pro
                        565                 570                 575

His Ser Cys His Arg Ala Gly Asn Asp Ala Pro Ala Gly Cys Leu Ser
                        580                 585                 590

Gln Ala Ala Arg Thr Pro Gly Asp Arg Thr Gly Thr Ser Lys Cys Arg
                        595                 600                 605

Lys Ala Gly Cys Val Tyr Phe Gly Thr Pro Glu Asn Lys Gly Phe Cys
                        610                 615                 620

Thr Leu Cys Phe Ile Glu Tyr Arg Glu Asn Lys His Phe Ala Ala Ala
        625                 630                 635                 640

Ser Gly Lys Val Ser Pro Thr Ala Ser Arg Phe Gln Asn Thr Ile Pro
                        645                 650                 655

Cys Leu Gly Arg Glu Cys Gly Thr Leu Gly Ser Thr Met Phe Glu Gly
                        660                 665                 670

Tyr Cys Gln Lys Cys Phe Ile Glu Ala Gln Asn Gln Arg Phe His Glu
                        675                 680                 685

Ala Lys Arg Thr Glu Glu Gln Leu Arg Ser Ser Gln Arg Arg Asp Val
                        690                 695                 700

Pro Arg Thr Thr Gln Ser Thr Ser Arg Pro Lys Cys Ala Arg Ala Ser
        705                 710                 715                 720

Cys Lys Asn Ile Leu Ala Cys Arg Ser Glu Glu Leu Cys Met Glu Cys
                        725                 730                 735

Gln His Pro Asn Gln Arg Met Gly Pro Gly Ala His Arg Gly Glu Pro
                        740                 745                 750

Ala Pro Glu Asp Pro Pro Lys Gln Arg Cys Arg Ala Pro Ala Cys Asp
                        755                 760                 765

His Phe Gly Asn Ala Lys Cys Asn Gly Tyr Cys Asn Glu Cys Phe Gln
                        770                 775                 780

Phe Lys Gln Met Tyr Gly
        785                 790

<210> SEQ ID NO 3
<211> LENGTH: 28
<212> TYPE: PRT
<213> ORGANISM: Homo sapiens

<400> SEQUENCE: 3

Trp Gly Val Gln Asp Thr Asp Leu Val Leu Arg Lys Ala Leu Phe Ser
1               5                   10                  15

Thr Leu Lys Glu Thr Asp Thr Arg Asn Phe Lys Phe
                20                  25

<210> SEQ ID NO 4
<211> LENGTH: 28
<212> TYPE: PRT
```

<213> ORGANISM: Rhesus rotavirus

<400> SEQUENCE: 4

Trp Gly Val Gln Asp Thr Asp Leu Val Leu Arg Lys Ala Leu Phe Ser
1               5                   10                  15

Thr Leu Lys Glu Thr Asp Thr Arg Asn Phe Lys Phe
            20                  25

<210> SEQ ID NO 5
<211> LENGTH: 28
<212> TYPE: PRT
<213> ORGANISM: Mus musculus

<400> SEQUENCE: 5

Trp Gly Val Gln Asp Thr Asp Leu Val Leu Arg Lys Ala Leu Cys Ser
1               5                   10                  15

Thr Leu Lys Glu Thr Asp Thr Arg Asn Phe Lys Phe
            20                  25

<210> SEQ ID NO 6
<211> LENGTH: 28
<212> TYPE: PRT
<213> ORGANISM: Canis lupus

<400> SEQUENCE: 6

Trp Gly Val Gln Asp Thr Asp Leu Val Leu Arg Lys Ala Leu Phe Ser
1               5                   10                  15

Thr Leu Lys Glu Thr Asp Thr Arg Asn Phe Lys Phe
            20                  25

<210> SEQ ID NO 7
<211> LENGTH: 28
<212> TYPE: PRT
<213> ORGANISM: Equus caballus

<400> SEQUENCE: 7

Trp Gly Ile Pro Asp Thr Asp Leu Val Leu Arg Lys Ala Leu Phe Ser
1               5                   10                  15

Thr Leu Lys Glu Thr Asp Thr Arg Asn Phe Lys Phe
            20                  25

<210> SEQ ID NO 8
<211> LENGTH: 28
<212> TYPE: PRT
<213> ORGANISM: Drosophila melanogaster

<400> SEQUENCE: 8

Trp Gly Val Gln Asp Ala Asp Leu Val Leu Arg Lys Ala Leu Ala Ser
1               5                   10                  15

Thr Leu Lys Glu Thr Asp Thr Arg Asn Phe Lys Phe
            20                  25

<210> SEQ ID NO 9
<211> LENGTH: 28
<212> TYPE: PRT
<213> ORGANISM: Philander opossum

<400> SEQUENCE: 9

Trp Gly Val Gln Asp Thr Asp Leu Val Leu Arg Lys Ala Leu Tyr Ser
1               5                   10                  15

Thr Leu Lys Glu Thr Asp Ile Arg Asn Phe Lys Phe
            20                  25

```
<210> SEQ ID NO 10
<211> LENGTH: 28
<212> TYPE: PRT
<213> ORGANISM: Ornithorhynchus anatinus

<400> SEQUENCE: 10

Trp Gly Val Gln Asp Thr Asp Leu Val Leu Arg Lys Thr Leu Phe Gly
1               5                   10                  15

Ala Leu Lys Glu Thr Asp Thr Arg Asn Phe Lys Phe
            20                  25

<210> SEQ ID NO 11
<211> LENGTH: 28
<212> TYPE: PRT
<213> ORGANISM: Zootoca vivipara

<400> SEQUENCE: 11

Trp Gly Val Gln Asp Val Asp Leu Val Leu Arg Lys Ala Leu Phe His
1               5                   10                  15

Ala Leu Lys Glu Val Asp Thr Arg Asn Phe Lys Leu
            20                  25

<210> SEQ ID NO 12
<211> LENGTH: 28
<212> TYPE: PRT
<213> ORGANISM: Gallus gallus

<400> SEQUENCE: 12

Trp Gly Ile Glu Asp Val Asp Leu Val Leu Arg Lys Thr Leu Phe Ser
1               5                   10                  15

Ala Leu Arg Glu Ile Asp Thr Arg Asn Phe Lys Leu
            20                  25

<210> SEQ ID NO 13
<211> LENGTH: 28
<212> TYPE: PRT
<213> ORGANISM: Gasterosteus aculeatus

<400> SEQUENCE: 13

Leu Gly Val Gln Asp Thr Asp Leu Val Leu Arg Lys Ala Leu His Gly
1               5                   10                  15

Val Leu Lys Glu Thr Asp Thr Gly Val Phe Arg Ala
            20                  25
```